(12) United States Patent
Reese et al.

(10) Patent No.: US 6,503,540 B1
(45) Date of Patent: Jan. 7, 2003

(54) CLONING AND CHARACTERIZATION OF BVES, A NOVEL GENE EXPRESSED IN HEART AND USES THEREOF

(76) Inventors: David E. Reese, 2006-A Natchez Trace, Nashville, TN (US) 37212; David M. Bader, 113 Cedar Creek Dr., Franklin, TN (US) 37067

( * ) Notice: Subject to any disclaimer, the term of this patent is extended or adjusted under 35 U.S.C. 154(b) by 0 days.

(21) Appl. No.: 09/535,909

(22) Filed: Mar. 24, 2000

Related U.S. Application Data

(60) Provisional application No. 60/126,087, filed on Mar. 25, 1999.

(51) Int. Cl.⁷ .................. A61K 35/34; A61K 35/44; A61K 49/00; C07H 21/04; C12Q 1/68
(52) U.S. Cl. .................. 424/569; 424/9.1; 424/9.3; 424/9.34; 424/9.341; 424/130.1; 424/93.2; 424/520; 536/23.1; 536/23.5; 536/29.3; 536/29.31; 536/26.33; 435/91.2; 435/91.4; 435/203; 435/320.1; 435/440
(58) Field of Search .................. 424/9.1, 9.3, 9.34, 424/9.341, 130.1, 93.2, 569, 520; 536/23.1, 23.5, 24.3, 24.31, 24.33; 435/6, 91.2, 91.4, 203, 320.1, 440

(56) References Cited

U.S. PATENT DOCUMENTS 5,582,979 A * 12/1996 Weber .................. 435/6

OTHER PUBLICATIONS

Harris et al. J. of The Am Society of Nephrology 6:1125–33, 1995.*
Ahn et al. Nature Genetics 3(4):283–91, 1993.*
Cawthon et al. Genomics 9(3):446–60, 1991.*
Lewin et al, Oxford University Press, p. 810, 1990.*
Abe etal. Cancer, 1992 (Mar. 1) 69(5) 1235–40.*

* cited by examiner

Primary Examiner—Mark Navarro
Assistant Examiner—Padmavathi V. Baskar
(74) Attorney, Agent, or Firm—Benjamin Aaron Adler

(57) ABSTRACT

The present invention is directed to cloning and characterization of bves (blood vessel/epicardial substance), a cDNA expressed in developing and adult heart and skeletal muscle cells in chick, mouse and human. Also provided are applications of Bves as a marker for cardiovascular or skeletal muscle diseases.

8 Claims, 18 Drawing Sheets

(10 of 18 Drawing Sheet(s) Filed in Color)

```
hbves   1                       ------------------------PPSNKTTCENWREI  14
mbves   1   MNSTESIPLAQSTYAGFTSELESLTPYPSNETTCENWREI  40
cbves   1   MDTTAISPLTP---LGYIPDLKNATSYPFNETACENWKEI  37 hbves  15   HHLYFHYANICFAYGLYIPTTLHLHMIFLRGMLTLGCTLF   54
mbves  41   HHLYFHYANYCFAYGLLIPTTLHLHMILLRYMLSLGCTLY   80
cbves  38   HHLYFHYANICFAAGLYIPTTLNLHMIFLRGLLTYGCALF   77 hbves  55   LYWATLYRCALDIMIWNSYFLGYNILHLSYLLYKKRPYKI   94
mbves  81   YYWATLYRCALDYMIWNSYFLGINILHLSYLLYKKRPYKI  120
cbves  78   IIWATLYRCALDIMIWNSYFLYYNLLHFIYLYYKRRPIKI  117 hbves  95   EKELSGMYRRLFEPLRYPPDLFRRLTGQFCMIQTLKKGQT  134
mbves 121   EKELGGYYHRLFEPLRYPPDLFRRLTGQFCMIQTLKRGQY  160
cbves 118   EKELSSLYKRMFEPLHYPPELFQRLTGQFCNIQTLKTGQA  157 hbves 135   YAAEDKTSYDDRLSILLKGKMKYSYRGHFLHNIYPCAFID  174
mbves 161   YATEDKTSYDDRLSILLKGRMKYSYRGHFLHNIYPCAFID  200
cbves 158   YAAEDKTSYDDRLSILLKGKMKYSYRGHFLHNIYPCAFID  197 hbves 175   SPEFRSTQMHKGEKFQYTIIADDNCRFLCWSRERLTYFLE  214
mbves 201   SPEFRSTQMHKGEKFQYTIYADDNCRFLCWSRERLTYFLE  240
cbves 198   SPEFRSTQMNRGEKFQYTIIADDKCKFLCWSRERLTYFLE  237 hbves 215   SEPFLYEIFRYLIGKDITNKLYSLNDPTLNDKKAKKLEHQ  254
mbves 241   SEPFLYEIFRYLIGKDITNKLYSLNDFTLNDKKYKKLEPQ  280
cbves 238   TEPFLYEIFKYLIGKDITNKLYSLNDPTLNDKASKKIDRQ  277 hbves 255   LSLCTQISMLEMRNSIASSSDSDDGLHQFLRGTSSMSSLR  294
mbves 281   MSLCTQISMLEMRNSITSSSDGEDGLHHFLRGSSSTASLP  320
cbves 278   PSLCSQLSYMQMRNSMARSSDSEDGLQMFLRGTSSSSSLR  317 hbves 295   --KLSQNQRASAKMKPIEEGAEDDDDYFEPASPNTLKYHQ  332
mbves 321   --MSSPQQRASAKMKPIEEGRR------------------  340
cbves 318   PGRTSPYLRTSAKMKPIEESYEDD--YFEAPSAEKLELQR  355 hbves 333   LP  334
mbves 341   --  340
cbves 356   LP  357
```

Fig. 3A

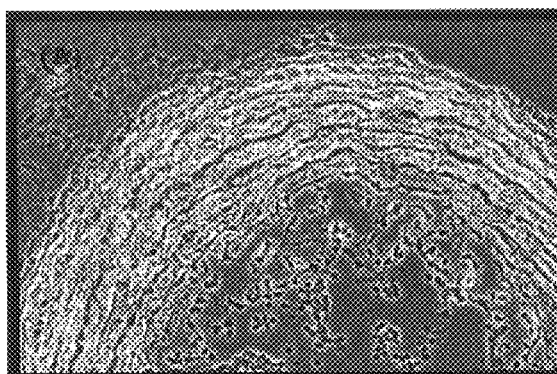
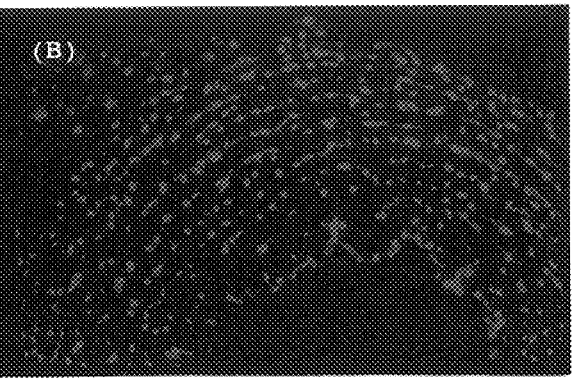
Fig. 12A
Fig. 12B
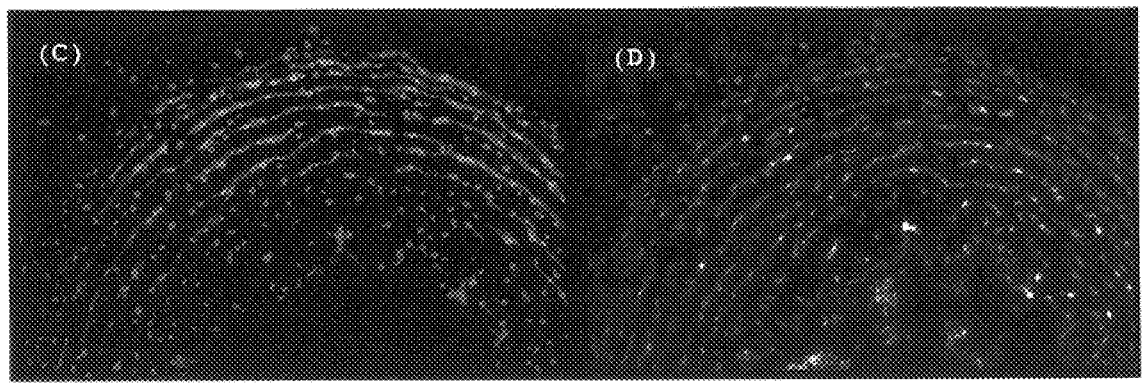
Fig. 12C
Fig. 12D

CLONING AND CHARACTERIZATION OF BVES, A NOVEL GENE EXPRESSED IN HEART AND USES THEREOF

CROSS-REFERENCE TO RELATED APPLICATION

This non-provisional patent application claims benefit of provisional patent application U.S. Serial No. 60/126,087, filed Mar. 25, 1999, now abandoned.

FEDERAL FUNDING NOTICE

The present invention was funded in part by training grant 1R01HL63325 to the Developmental Biology Program (NIHCHD). Consequently, the United States government has certain rights in this invention.

BACKGROUND OF THE INVENTION

1. Field of the Invention

The present invention relates generally to the fields of developmental biology and molecular biology. More specifically, the present invention relates to the cloning and expression of a novel gene, bves, whose nucleic acid sequence encodes a blood vessel/epicardial substance, Bves, protein involved in cardiovascular or skeletal muscle diseases.

2. Description of the Related Art

Diverse cell types including myocytes, endocardial endothelial cells (hereafter referred to as endocardium), fibroblasts, epicardium, vascular endothelium and vascular smooth muscle make up the heart (Fishman and Chien, 1997). These cells populate the heart at different times and have diverse. origins. Myocytes and endocardium arise from epithelia located in the anterior lateral mesoderm of the embryo and are the first cells to comprise the heart (DeHann, 1965; Coffin and Poole, 1988; Sater and Jacobson, 1989; Gonzalez-Sanchez and Bader, 1990; Fishman and Chien 1997). After establishment of this two-layered epithelial tube, additional migratory mesenchymal cells move into the forming heart. Among these are neural crest cells that are targeted to specific regions of the outflow tract and cardiac skeleton where they differentiate into connective tissue and smooth muscle (Kirby et al, 1978; Kirby and Waldo, 1990) and cells of the proepicardial organ that will differentiate into at least four different cell types.

The proepicardial organ is a transitory epithelial structure located at the septum transversum (Manasek 1968). At stage 15 in the chick and 9.5 dpc in the mouse, the proepicardial organ is situated at the root of the sinoatrium on its dorsal surface (Manasek, 1968; Komiyama et al, 1987). Strands of epithelium begin to extend over the heart forming the future epicardium while the future pericardium is formed as the proepicardial strands extend over the pericardial cavity (Manasek, 1968; Manner, 1993). A subpopulation of epicardial cells begins to delaminate and migrate into the subepicardial connective tissue and myocardium (Manasek, 1968; Viragh and Challice 1981; Hiruma and Hirakow 1989; Manner 1993). These cells will differentiate into fibroblasts, vascular endothelium and vascular smooth muscle (Mikawa and Gourdie, 1996; Dettman et al, 1998). While clonal analysis has shown that divergence of these lineages likely has already taken place in the proepicardial organ (Mikawa and Gourdie, 1996; Dettman et al, 1998), the timing of commitment, differentiation and patterning of endothelial and smooth muscle cells is unresolved.

Development of the intracardiac circulation is unique in vasculogenesis. Most of the systemic vessels develop from a vast endothelial sheet that is connected to the endocardium of the developing heart (Coffin and Poole, 1988). Recent studies suggest that endothelial cells induce local mesenchyme to differentiate into smooth muscle (Folkman and D'Amore, 1996 and references within). Development of the intracardiac vessels contrasts this situation as endothelial and smooth muscle cell progenitors arise from the same epithelial structure (the proepicardial, organ; Manasek, 1968; Viragh and Challice, 1981; Mikawa and Gourdie, 1996; Dettman et al, 1998). These epithelial cells delaminate, migrate as single cells to distant sites within the heart and then differentiate. In addition, the intracardiac system is generated without connection to the systemic circulation (Poelmann et al, 1993; Viragh et al. 1993). Finally, a new bHLH molecule, capsulin, has been identified in the progenitors of smooth muscle of the intracardiac arterial system suggesting unique molecular regulation (Hidai et al, 1998; Lu et al, 1998). Thus, the ontogenesis of the intracardiac arterial system appears to be unique.

Organogenesis of the heart is a complex process where several independent yet interacting morphogenetic events proceed concurrently. Specific cellular process involved in heart development is not yet known. The prior art is deficient in the lack of a heart enriched cDNA library. Further, the prior art is deficient in the lack of identification and characterization of bves, a novel gene whose nucleic acid sequence is expressed in developing and adult heart and skeletal muscle. The present invention fulfills this longstanding need and desire in the art.

SUMMARY OF THE INVENTION

The present invention screens for novel gene products expressed during heart organogenesis and describes the identification and characterization of a novel gene product, Bves (Blood Vessel/Epicardial Substance). Bves is uniquely expressed in the proepicardial organ and a subset of its progeny gives rise to the vascular smooth muscle of the intracardiac arteries. Analysis of Bves expression reveals the migration and patterning of vascular smooth muscle in the heart and possible insights into the cellular regulation of smooth muscle differentiation during vasculogenesis.

The present invention discloses that bves is a novel mRNA expressed in the developing heart in chick (cbves), mouse (mbves) and human (hbves). cDNA sequences of cbves, mbves and hbves are shown in SEQ ID No. 1, SEQ ID No. 2 and SEQ ID No. 3, respectively, and deduced amino acid sequences in SEQ ID No. 4, SEQ ID No. 5 and SEQ ID No. 6, respectively. bves is highly conserved between all three species at the amino acid level with 75% identity and 92% similarity.

In one embodiment of the present invention, there is provided a nucleic acid sequence encoding a Bves protein, wherein said sequence is selected from the group consisting of: (a) a nucleic acid which encodes a Bves protein; (b) a nucleic acid which is complementary to the nucleic acid of (a) encoding a Bves protein; and (c) a nucleic acid differing from the nucleic acids of (a) and (b) in codon sequence due to the degeneracy of the genetic code, and (d) a nucleic acid of (a), (b) or (c) and which is either DNA or RNA. Specifically, the gene whose nucleic acid sequence is expressed in developing and adult heart and skeletal muscle cells in an organism is selected from the group consisting of chick, mouse and human. More specifically, the nucleic acid sequence comprises a cDNA sequence selected from the group consisting of SEQ ID Nos. 1–3, while the Bves protein has an amino acid sequence selected from the group consisting of SEQ ID Nos. 4–6.

In another embodiment of the present invention, there is provided an expression vector which expresses the desired nucleic acid when the vector is introduced into a cell.

In still another embodiment of the present invention, there is provided a host cell transfected with the vector which expresses a Bves protein. Preferably, the host cell can be a bacterial cell, an animal cell, a plant cell or an insect cell. Preferably, the bacterial cell is *E. coli* cell. More preferably, the host cell is the HT-1-bves engineered cell line.

In yet another embodiment of the present invention, there is provided an isolated and purified Bves protein coded for by a nucleic acid sequence selected from the group consisting of: (a) a nucleic acid which encodes a Bves protein; (b) a nucleic acid complementary to the nucleic acid of (a) which encodes a Bves protein; and (c) a nucleic acid differing from the genes of (a) and (b) in codon sequence due to the degeneracy of the genetic code, and which encodes a Bves protein and (d) a nucleic acid of (a), (b) or (c) and which is either DNA or RNA. Preferably, the Bves protein has an amino acid sequence selected from the group consisting of SEQ ID Nos. 4–6.

In still yet another embodiment of the present invention, there is provided a recombinant protein having an amino acid sequence selected from the group consisting of SEQ ID Nos. 4–6. Preferably, the amino acid sequence is encoded by a nucleic acid sequence selected from the group consisting of SEQ ID Nos. 1–3. Preferably, the recombinant protein is an antigen.

In yet another embodiment of the present invention, there is provided a method of producing the recombinant protein, comprising the steps of obtaining a vector that comprises an expression region comprising a sequence encoding the amino acid sequence selected from the group consisting of SEQ ID Nos. 4–6 operatively linked to a promoter; transfecting the vector into a cell; and culturing the cell under conditions effective for expression of the expression region.

In still yet another embodiment of the present invention, there are provided antibodies immunoreactive with an amino acid sequence shown in SEQ ID No. 6.

The invention may also be described in certain embodiments as a method of detecting development of coronary vessels in an individual, comprising the steps of applying the antibody to the individual; and detecting the localization of the antibody. If the localization is detected in coronary vascular smooth muscle cells, the testing individual has developed coronary vessels.

The invention may also be described in another embodiment as a method of detecting a cardiovascular disease in an individual by applying the antibody and then detecting the localization of the antibody in the individual. If the localization is not detected in cardiovascular smooth muscle cells, the testing individual is suspected to have a cardiovascular disease. An example of such cardiovascular disease is atherosclerosis.

Similarly, the invention may also be described in still another embodiment as a method of detecting a skeletal muscle disease in an individual by detecting the immunolocalization of the antibody in skeletal muscle cells. Negative result indicates the possible existence of skeletal muscle disease in the testing individual. Examples of such skeletal muscle disease are muscular dystrophy and myonic dystonia.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3A shows the comparison of derived amino acid sequence shown in human, mouse and chicken Bves in the conserved carboxyl domain (SEQ ID Nos. 6–8). Black bars above the sequence show predicted transmembrane domains. Amino acid sequence was obtained using at least two independent clones over the entire length of the cDNAs.

FIG. 7 shows immunolocalization of Bves to the proepicardial organ and migrating proepicardial strands.

FIG. 8 shows that anti-Bves marks the epicardium and is competed by immune peptide. Sections of day 7 hearts were reacted with anti-Bves in the presence or absence of competing peptide.

FIG. 9 shows epicardial and subcellular localization of Bves positive cells in the E5 chick heart.

FIG. 10 shows immunolocalization of Bves to developing intracardiac arteries.

FIG. 12 shows Bves protein localization within the media of the proximal aorta. FIG. 12A shows phase contrast view of a transverse section through a E19 chick aorta. FIG. 12B shows Bves immunolocalization in the E19 aorta. FIG. 12C shows colocalization of Bves (red) and alpha smooth muscle actin (green) in the media of the developing aorta demonstrating that Bves-positive, alpha actin-negative cells are located medially to smooths muscle cells that express both proteins. FIG. 12D shows subcellular distribution of Bves in the aorta. Colocalization of Bves with DAPI (blue) shows a perinuclear distribution. (250×)

FIG. 13 shows that Bves expression is induced by cardiac muscle. FIGS. 13A and 13D show the proepicardial cells stained with DAPI to show the location of the nuclei. In FIGS. 13B and 13E, alpha smooth muscle actin localization (green) of these cells shows which cells are committed to the smooth muscle lineage. FIGS. 13C and 13F shows the results of staining with anti-Bves antibody. The Bves positive proepicardial cells (red) grown in the presence of cardiac muscle show strong staining for BVES, while in the absence of cardiac muscle, Bves staining is greatly diminished (FIG. 13F).

DETAILED DESCRIPTION OF THE INVENTION

Figure 1A:
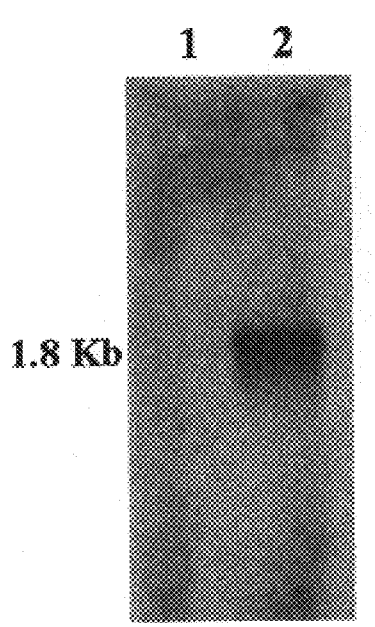
FIG. 1 shows Northern blot analysis of bves expression in chick. 20 μg of RNA from stage 20 heartless embryos (lane 1) and hearts (lane 2) was probed with the original PCR fragment used to clone bves (FIG. 1A). Poly (A)+RNA (2 μg/lane) isolated from various tissues of an E14 chick (FIG. 1B). RNA was probed using a 300 bp fragment of bves. Tissues shown are heart (lane 1), brain (lane 2), liver (lane 3), gizzard (lane 4), and skeletal muscle (lane 5). For a loading control blot was stripped and reprobed with a 250 bp cDNA probe for gapdh.

The present invention provides a subtractive method to clone novel messages enriched in the heart. One such message, bves (Blood vessel/epicardial substance) is a novel protein that is highly conserved among chicken, mouse and human. The bves message is detected at high levels in early chick hearts. Using anti-Bves antibodies, bves is shown to be expressed in cells of the proepicardial organ, migrating epicardium, epicardial-derived mesenchyme and smooth muscle of the developing intracardiac arterial system including the coronary arteries. The data suggest that Bves is an early marker of developing vascular smooth muscle cells. In addition, the expression pattern of Bves protein reveals the patterning of intracardiac vascular smooth muscle and possible insights into the cellular regulation of smooth muscle differentiation during vasculogenesis.

bves is a novel mRNA expressed in the developing heart in chick and mouse. Northern and dot blot analyses reveal restricted expression of bves in the heart and skeletal muscle in the embryo and adult in human (hbves). BLAST searches of the NCBI databases predicted that hbves is novel and has an exact match with a genomic PAC 52202 that localizes to chromosome 6q21. Computer conformation analysis predicts three transmembrane helices with an extracellular C-terminus that is conserved in chick, mouse and human. bves is highly conserved between all three species at the amino acid level with 75% identity and 92% similarity.

In one embodiment of the present invention, there is provided a nucleic acid sequence encoding a Bves protein, wherein such nucleic acid sequence is selected from the group consisting of: (a) a nucleic acid sequence which encodes a Bves protein; (b) a nucleic acid sequence which complements and hybridizes to the nucleic acid sequence of (a) and which encodes a Bves protein; and (c) a nucleic acid sequence differing from the nucleic acid sequences of (a) and (b) in codon sequence due to the degeneracy of the genetic code, and which encodes a Bves protein. Specifically, the nucleic acid sequence of the gene encoding the Bves protein is expressed in developing adult heart and skeletal muscle cells in an organism selected from the group consisting of chick, mouse and human. More specifically, the nucleic acid sequence comprises a cDNA sequence selected from the group consisting of SEQ ID Nos. 1–3, while the Bves protein has an amino acid sequence selected from the group consisting of SEQ ID Nos. 4–6.

In another embodiment of the present invention, there is provided an expression vector capable of expressing the nucleic acid sequence in question when the vector is introduced into a cell.

In still another embodiment of the present invention, there is provided a host cell transfected with the vector which expresses a Bves protein. Preferably, the host cell can be a bacterial cell, an animal cell, a plant cell or an insect cell. Preferably, the bacterial cell is *E. coli* cell. More preferably, the host cell is the HT-1-bves engineered cell line.

In yet another embodiment of the present invention, there is provided an isolated and purified Bves protein coded for by a nucleic acid sequence selected from the group consisting of: (a) a nucleic acid sequence which encodes a Bves protein; (b) a nucleic acid sequence which complements and hybridizes to the nucleic acid sequence of (a) and which encodes a Bves protein; and (c) a nucleic acid sequence differing from the nucleic acid sequences of (a) and (b) in codon sequence due to the degeneracy of the genetic code, and which encodes a Bves protein. Preferably, the Bves protein has an amino acid sequence selected from the group consisting of SEQ ID Nos. 4–6.

In still yet another embodiment of the present invention, there is provided a recombinant protein having an amino acid sequence selected from the group consisting of SEQ ID Nos. 4–6. Preferably, the amino acid sequence is encoded by a nucleic acid sequence selected from the group consisting of SEQ ID Nos. 1–3. Preferably, the recombinant protein is an antigen.

In yet another embodiment of the present invention, there is provided a method of producing the recombinant protein, comprising the steps of obtaining a vector that comprises an expression region comprising a nucleic acid sequence encoding the amino acid sequence selected from the group consisting of SEQ ID Nos. 4–6 operatively linked to a promoter; transfecting the vector into a cell; and culturing the cell under conditions effective for expression of the expression region.

In still yet another embodiment of the present invention, there are provided antibodies immunoreactive with an amino acid sequence shown in SEQ ID No. 6.

The invention may also be described in certain embodiments as a method of detecting development of coronary vessels in an individual, comprising the steps of applying the antibody to the individual; and detecting the localization of the antibody. If the localization is detected in coronary vascular smooth muscle cells, the testing individual has developed coronary vessels.

The invention may also be described in another embodiment as a method of detecting a cardiovascular disease in an individual by applying the antibody and then detecting the localization of the antibody in the individual. If the localization is not detected in cardiovascular smooth muscle cells, the testing individual is suspected to have a cardiovascular disease. An example of such cardiovascular disease is atherosclerosis.

Similarly, the invention may also be described in still another embodiment as a method of detecting a skeletal muscle disease in an individual by detecting the immunolocalization of the antibody in skeletal muscle cells. Negative result indicates the possible existence of skeletal muscle disease in the testing individual. Examples of such skeletal muscle disease are muscular dystrophy and myonic dystonia.

The following examples are given for the purpose of illustrating various embodiments of the invention and are not meant to limit the present invention in any fashion.

EXAMPLE 1

Animals and Tissues

Fertilized White Leghorn chicken and quail eggs were obtained from Truslow Farms (Chestertown, Md.) and incubated under high humidity in a 37° C. incubator. Embryos were staged according to Hamburger and Hamilton (1951). Timed pregnant ICR mice were obtained from the Jackson Lab and embryos were dissected at various days post coitus. For RNA isolation, embryos were dissected and excised tissues were immediately frozen on dry ice. All tissues were stored at −70° C. prior to RNA preparations.

EXAMPLE 2

RNA Isolation

For the production of a heart enriched cDNA library, RNA was prepared from frozen tissues (HH stage 18 hearts and embryos without hearts). Samples were sonicated in Trizol reagent (Life Technologies) and prepared as per manufacturer's instructions. Poly (A)+ mRNA was twice enriched using the Poly A+ Tract System oligo dT immunomagnetic separation (Promega).

EXAMPLE 3 cDNA Library Construction and Screening

A Stage 18 Heart subtracted library was constructed using PCR Select (Clontech) as per manufacturer's instructions. Briefly, 1 μg twice Poly (A)+ enriched RNA was used to synthesize double stranded cDNA from heart and heartless embryos. The resulting cDNA was RsaI digested and the heart cDNA was separated into two pools, where different adaptors were ligated to each set. Two different subtracted pools were created by hybridizing both heart pools to non-adaptor ligated embryonic cDNA. One subsequent round of subtraction was carried out by combining these pools. The resulting hybridization mixture was used as template to PCR amplify differentially expressed cDNA using adapter specific primers. The differentially expressed cDNAs were then cloned into T-easy vector (Promega). The sequence complexity of this library was approximated to be 2500 with an average insert size of 350 bp. Analysis of 120 independent clones indicated that the known sequences obtained were indeed enriched in the heart at this stage in development.

EXAMPLE 4

Cloning of Chick and Mouse Bves

Chick bves was cloned using the original cloned cDNA insert as a probe. Library screening was performed using a chick embryonic heart library (Wei et al 1996). Three independent overlapping cDNA clones were sequenced and compared to the NCBI database by BLAST homology searching. The longest of these clones, pbves.1 contains a 1.6 kb insert within the pEXlox vector. Multiple attempts at 5' end cloning using RACE failed to provide additional sequence.

Mouse ESTs were identified by sequence similarity with the pbves.1 clone. The longest independent clone 1181026, (Genome systems) contains 1.4 kb of mbves. cDNA library screening of a lambda mouse heart library (Stratagene) failed to yield larger cDNA clones. 5' RACE of a mouse heart RACE library (Clontech) yielded 300 bp of additional sequence at the 5' end of the cDNA. Sequence analysis of bves clones was performed using Macvector 6.5 (Oxford Molecular Group). Sequence homology analysis of mouse and chick bves was performed using a Clustal Alignment designated by the program.

EXAMPLE 5

Cloning of Human Bves

In order to clone the human homologue of bves, a relaxed stringency PCR approach (50° C. annealing on a 58° C. primer) was used. Since chick and mouse bves share a high percentage similarity in their C-terminal domains, primers (5' Primer sequence TTTGAACCA CTCCGAGTCCCTCC, SEQ ID No. 9; 3' Primer sequence TGACCAGCA TAAGAACCTGCAG, SEQ ID No. 10) from mbves were used to amplify a 250 bp fragment from a human heart cDNA library (Stratagene). This fragment was sequenced and found to be highly homologous to the previously cloned chick and mouse bves. This cDNA was then used to screen for larger clones from the same cDNA library. Two identical 1.9 kb clones were obtained, sequenced and used to BLAST the NCBI databases. A human genomic PAC 52202 (Genbank Accession number Z95329) was identified that maps to chromosome 6q21. The cDNA sequence was an exact match with intervening sequences that mark the intron-exon boundaries of the gene. Since this region of human chromosome 6 is syntenic with mouse chromosome 10, it is likely that the cloned mouse homologue localizes to chromosome 10.

EXAMPLE 6
Northern Blot Analysis

Equal amounts of poly (A)+ RNA (2 µg) were loaded in a 1% formaldehyde denaturing gel for electrophoresis. After electrophoresis, RNA was transferred to a charged nylon membrane (Genescreen), crosslinked and prehybridized using Rapid Hyb buffer (Amersham) at 65° C. for at least two hours. Membranes were hybridized to $^{32}$P labeled random primed cDNA probes. Probes used include PCR probes generated specifically to bves and β-actin.

EXAMPLE 7
RT-PCR Analysis of Bves Expression in Staged Embryo Series

Total RNA was isolated from cardiogenic regions of stage 4–8 embryos and from hearts of stage 10–18 embryos using Trizol reagent. For mouse embryos, total RNA was prepared in the same manner for whole embryos at different time points. 100 ng of total RNA was used to amplify bves, vmhc1 and gapdh using gene specific primers. The primers used for bves were 5'-AACCACTCCATGTGCCTCCA-3' (SEQ ID No. 11) and 5'-CTGCGATAATGGTGACCTGG-3' (SEQ ID No. 12). The primers used for vmhc1 were described previously (Bisaha and Bader, 1991). An initial 45° C. first stand synthesis was performed for 45 minutes followed by thirty cycles of PCR with the following conditions: 94° C. for 10 seconds, 52° C. for 10 seconds, and 45 seconds extension at 72° C. with RT-Access RT-PCR (Promega). Products were electrophoresed on a 1% agarose gel and blotted to a charged nylon membrane for Southern analysis. The resulting membranes were probed using radiolabeled random primed cDNA inserts from clones corresponding to bves, mbves, vmhc1 and gapdh.

EXAMPLE 8
In situ Hybridization Using Bves Probes

Mouse 8.0, 9.5, 12.5 dpc embryos were used for in situ hybridization. In situ hybridizations were carried out as described previously (Ausbel et al., 1998). Briefly, a 3' probe (SEQ ID No. 13) was generated from the mouse cDNA mbves.2, which corresponds t o the 3' UTR and 3' most portion of the mbves ORF. Embryos were isolated at 8.5, 10.5 and 12.5 dpc and subjected to hybridization as described (Ausbel et al., 1998).

EXAMPLE 9
Polyclonal Antibody Generation

Polyclonal antibody D033 was generated in rabbits (Biosynthesis). The chick Bves sequence used was DSPE-FRSTQMNRGEK (SEQ ID No. 14). This peptide was used to preabsorb antisera in competition assays. Antisera production was standard and affinity purified antiserum was produced with peptide conjugated column.

EXAMPLE 10
Immunolocaliztion of Bves Using D033 Polyclonal Antibody

Immunofluorescence staining was carried out using frozen sections (8 µm) of staged chick embryos. All sections were fixed in 70% methanol, permeabilized in PBS with 0.25% Triton X-100 and blocked for at least 2 hours in 2% BSA/PBS. Antibodies were reacted for 1–2 hours followed by standard PBS washes, second antibody reaction for 1 hour, PBS washes and post-fixation. Dilutions of primary antibodies were: D033 polyclonal anti-Bves 1:100, mAb anti smooth muscle alpha actin 1:100 (Sigma), MF20 undiluted hybridoma supernatant, QH1 1:1000 dilution of mouse ascites (DSHB) in 1% BSA/PBS. Secondary antibodies used were obtained from the Jackson Immunoresearch and were raised against either Rabbit or Mouse IgG and conjugated to either Cy2 or Cy3 at suggested dilutions. Sections were also stained with DAPI to identify nuclei at a dilution of 1:2000. At least 10 sections in five separate experiments were examined for each stage with each antibody. For peptide competitions, a 50 molar excess of immune peptide was added for one hour prior to reaction with the sections. All subsequent steps were identical.

For western blot analysis, stage 25 hearts were collected, solubilized in SDS sample buffer, and subjected to SDS/PAGE and transfer to PVDF paper (Amersham) using standard methods (Harlow and Lane, 1988). Blots were blocked in 2% non-fat dry milk in PBS and reacted with anti-Bves (1:100) in 2% non-fat dry milk for 4 hours. Blots were washed, reacted with AP-labeled goat-anti-rabbit (1:10,000, Jackson Laboratories) and developed as previously described (Harlow and Lane, 1988). The molecular weight of the reactive band was calculated by comigration with molecular weight standards (BioRad). For peptide competition, anti-Bves was reacted with 50 molar excess of immune peptide for 1 hour prior to reaction with the blotted filters.

It should be noted that in addition to the cells of the intracardiac arterial system and proximal aorta, this antibody recognizes a protein in the smooth muscle of the developing gut. As bves message is not detected in this tissue, it was assumed that anti-Bves sera recognizes a related protein in intestinal smooth muscle. Efforts are underway to clone this message.

EXAMPLE 11
Identification and Predicted Structure of Novel Cardiac-Specific Gene Products To identify novel heart-enriched messages expressed during cardiac morphogenesis, the "looping" stage of heart development was chosen because several critical events such as looping, myocyte proliferation, trabeculation, valve formation, and epicardial differentiation occur at this time. A cDNA library enriched for heart-specific sequences was produced (approximately 2,500 independent clones, average insert size of 350 bp). 120 clones were randomly selected, sequenced and blasted against known databases. Over 70% of the clones isolated were known muscle- or cardiac-specific messages, primarily structural gene products. It should be noted that the only differentiated myocytes in the stage 18 chick embryo, outside the heart, are myotomal cells that comprise a minor cell population.

Figure 1B:
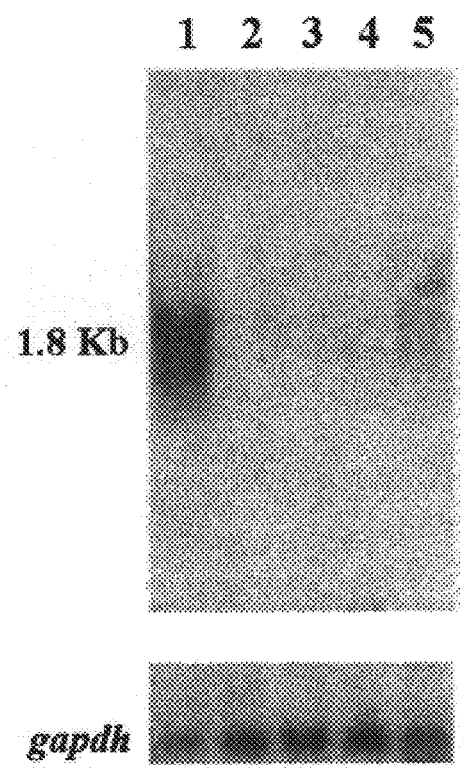

The sequences of 12 clones were unique. These inserts were used in RNA blot analysis to determine which RNAs were enriched in the heart. The hybridization pattern of bves with stage 20 heart and embryo without the heart RNAs is shown in FIG. 1A. bves hybridized to a 1.8 Kb band enriched in the heart and not detectable at high levels in the rest of the embryo. Northern analysis of day 14 chicken embryos shows that bves expression is maintained at high levels in the heart (FIG. 1B). While Northern analysis determined that bves is highly enriched in the heart, the protein expression data suggest that bves is also expressed in the proximal aorta (see below). Analysis of EST databases identified related mouse cDNAs that were obtained and used to clone homologues from corresponding mouse heart cDNA libraries.

Figure 2A:
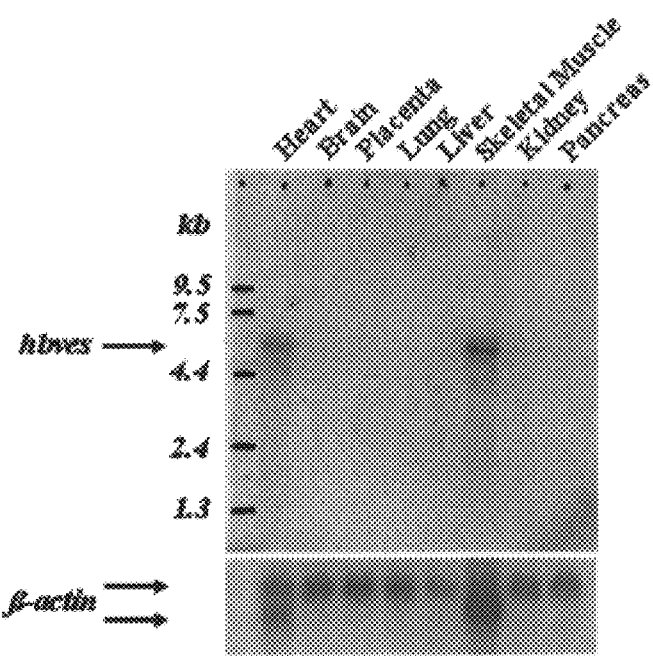
FIG. 2A shows Northern blot analysis of adult tissues demonstrating hbves expression in heart and skeletal muscle. β-actin hybridization shows a loading control.
Figure 2B:
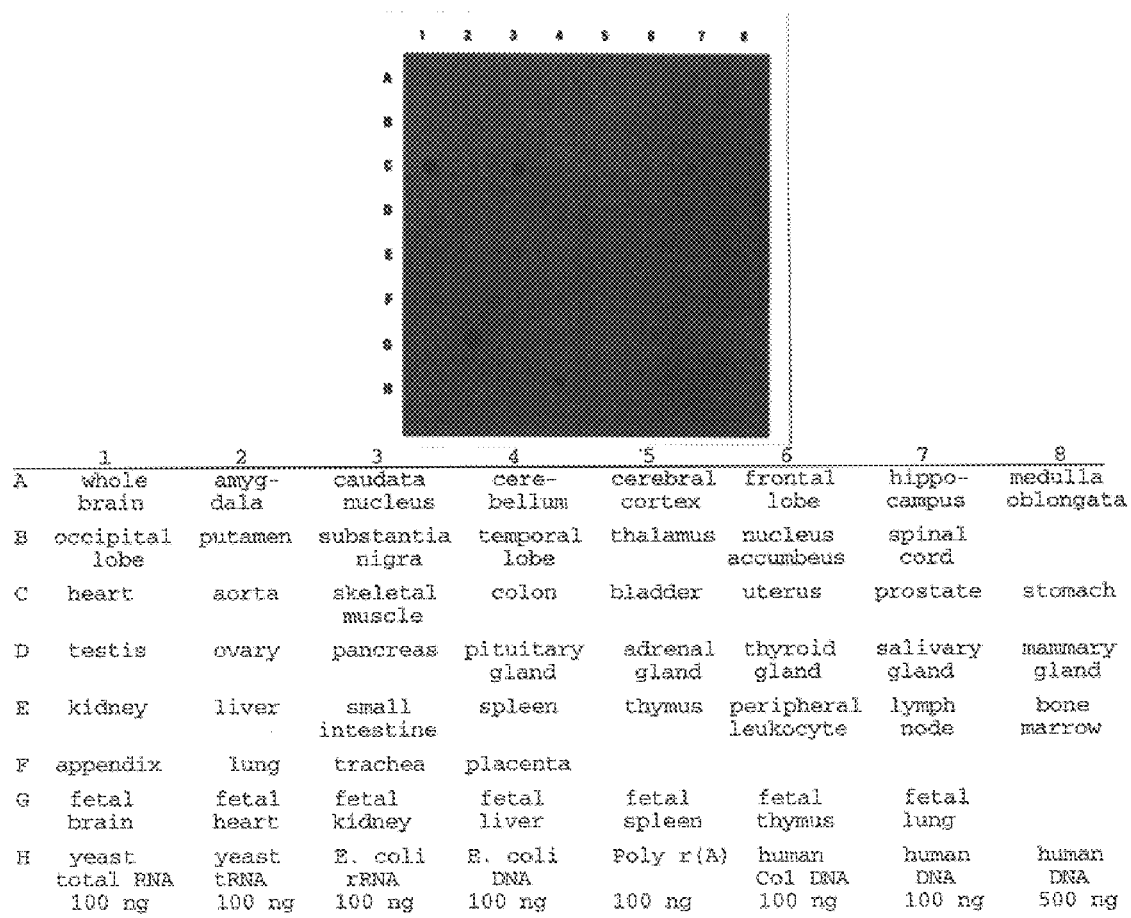
FIG. 2B shows dot blot analysis demonstrating hbves expression in adult heart (C1), adult skeletal muscle (C3) and fetal heart (G2).

To determine whether the novel human mRNA was expressed in a similar manner, a Multiple Tissue Northern (Clontech) (Liew et al, 1994; Spanakis, 1993; Spanakis and Brouty-Boye, 1994) was probed with the original 250 bp hbves cDNA fragment and washed at high stringency (0.1× SSC, 0.1% SDS, 65° C.). Expression was only seen in the heart and skeletal muscle of the adult (FIG. 2A). To define more precisely which tissues express hbves, a human tissue was probed for dot blot (Clontech) (Liew et al, 1994; Spanakis, 1993; Spanakis and Brouty-Boye, 1994) with the same 250 bp random primed probe and washed at high stringency. The hybridization pattern confirmed the Northern analysis and also showed hbves expression in the fetal heart (FIG. 2B).

Figure 3B:
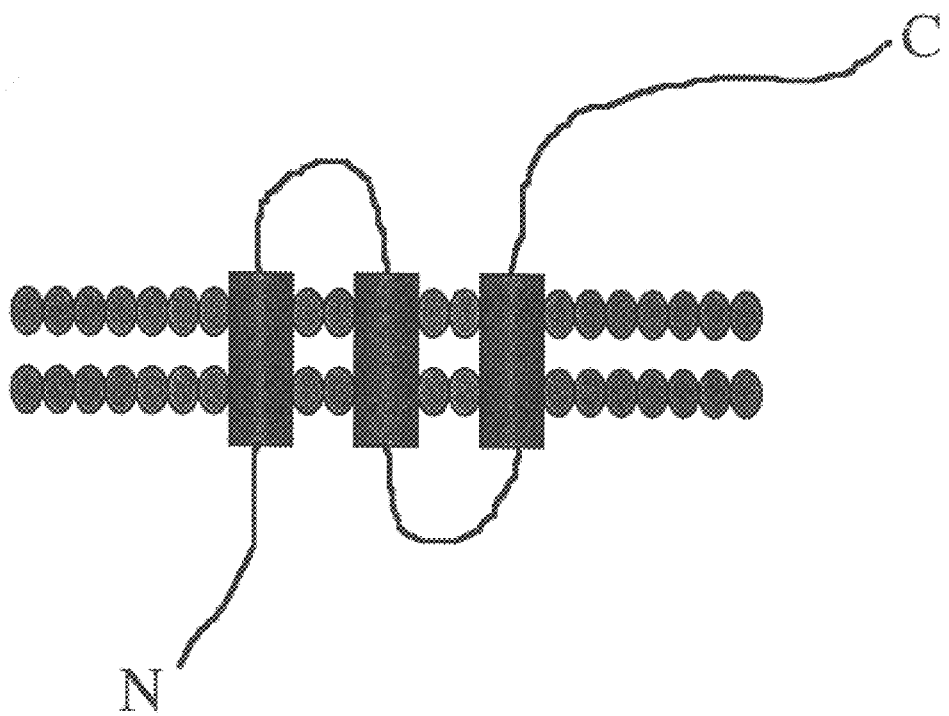
FIG. 3B shows the predicted topology of Bves as determined by computer analysis shows the position of N- and C-termini and three transmembrane domains.

The derived amino acid sequences of chicken, mouse and human Bves are given in FIG. 3A. Derived amino acid sequences demonstrate a high degree of homology, especially over amino acids 70 to 472 in the two predicted sequences. There is 75% identity and 92% similarity in this region (FIG. 3A). The N-terminal most 70 amino acids represent the most divergent portion of the predicted protein. Computer analysis predicts a conserved overall topography among avians, mammals and humans. Three possible transmembrane domains with an extracellular C-terminal region are predicted as well as multiple phosphorylation and glycosylation sites (FIG. 3B). No other known motifs are present in this region of the predicted protein. Analyses done so far do not prove that any of these predicted structures have functional significance. A search of Genbank also shows no significant homology with. any other known proteins. These data show that Bves is a novel yet highly conserved protein.

EXAMPLE 12
Bves Message is Highly Expressed in the Developing Heart

Figure 4:
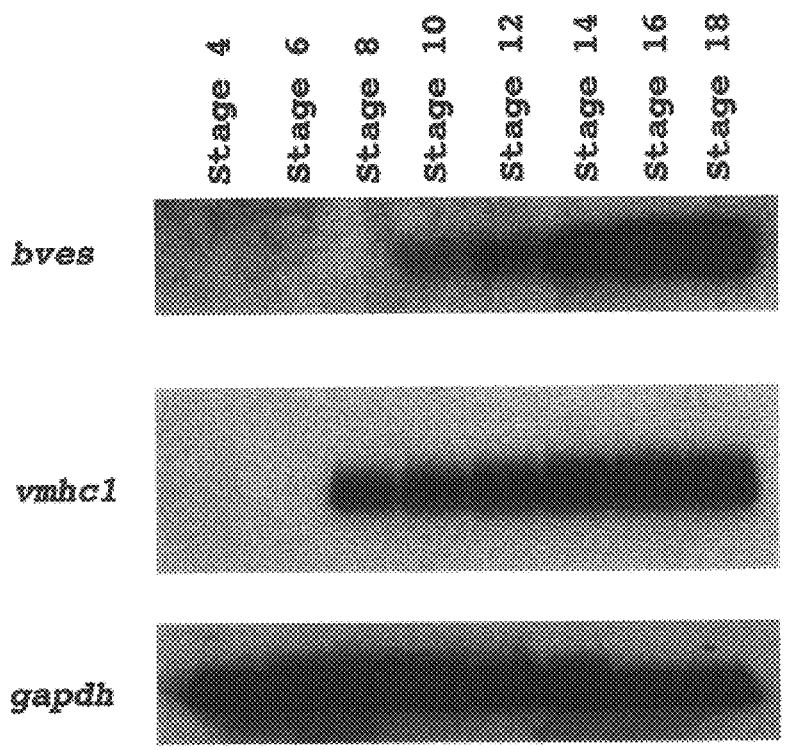
FIG. 4 shows temporal expression of bves in the developing chick. bves, vmhc1, and gapdh specific primers were used to detect expression via RT-PCR. Products were then electrophoresed, Southern blotted and probed using gene specific sequences. Stages of embryos used are indicated above each lane.

Northern blot analysis determined that a single band hybridized with the bves probe in the differentiated heart (FIG. 1). bves expression is maintained throughout heart development and in the adult. To determine when bves expression is first detected during cardiogenesis, staged cardiogenic mesoderm and hearts were isolated and prepared for RT/PCR analysis. GAPDH was used as a positive control while VMHC1 was used as a marker for the initiation of myogenic differentiation (Bisaha and Bader, 1991). As seen in FIG. 4, VMHC1 expression is detected at stage 8 marking the onset of contractile protein. gene expression in the avian heart. Other studies have shown that the major contractile protein genes are also activated during this time frame (Ruzicka and Schwartz, 1988; Bisaha and Bader, 1991; Han et al, 1992). Interestingly, bves is first detected at stage 10 suggesting that its expression is not activated with the major contractile protein genes.

EXAMPLE 13
In situ Hybridization to Mouse Embryos

Figure 5:
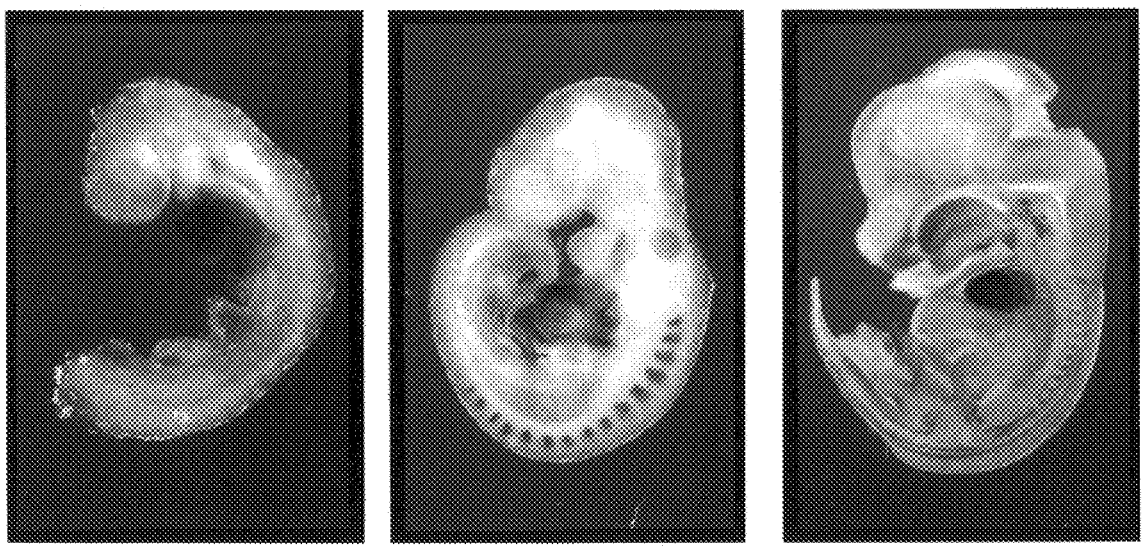
FIG. 5 shows in situ hybridization using mbves specific probes. Mouse embryos used are 8.0, 9.5 and 12.5 dpc embryos.

The result of in situ hybridization is shown in FIG. 5. This pattern of in situ hybridization clearly demonstrates that at the mRNA level, mbves is expressed throughout the heart and myotome of the developing embryo. Since skeletal muscle eventually expresses mbves, it is reasonable that the myotome expresses mbves.

Figure 6:
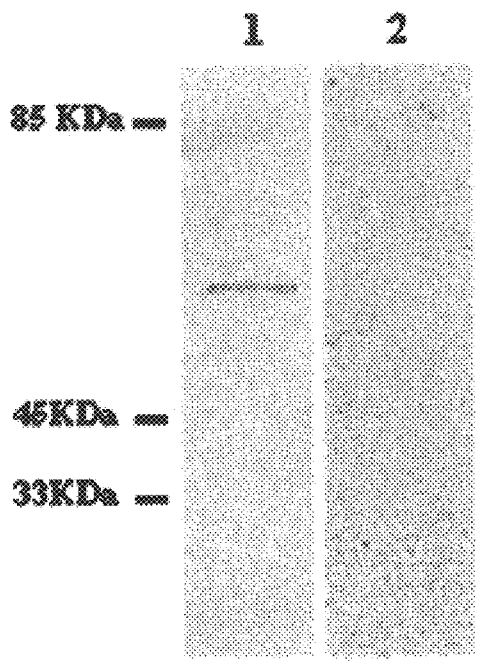
FIG. 6 shows Western blot analysis with anti-Bves. 150 μg of total protein was loaded on 12% gel. Anti-Bves reacts with a single band at approximately 58 kD (lane 1). This band is competed by pretreatment of serum with a 50 molar excess of immune peptide (lane 2).

EXAMPLE 14
Bves Protein is Expressed in the Proepicardial Organ, Migrating Epicardial Cells and Vascular Smooth Muscle In order to determine the cellular distribution of Bves protein during the initial phases of heart development, an antiserum against chicken Bves was produced. This antiserum reacted with a single band calculated to be approximately 58 kD in western analysis of stage 25 hearts (FIG. 6, lane 1). This is compared to the predicted molecular weight of 53 kD for unmodified Bves derived from cDNA sequencing. The immunoreactive band was specifically competed by excess of the immune peptide (FIG. 6, lane 2). This immunoreactive band is not seen in blots of other tissues (data not shown). It should be noted that 150 $\mu$g of total heart protein were loaded on this gel and that the band appears to represent a minor component of the total protein compliment in the heart.

Figures 7A, 7B, 7C:
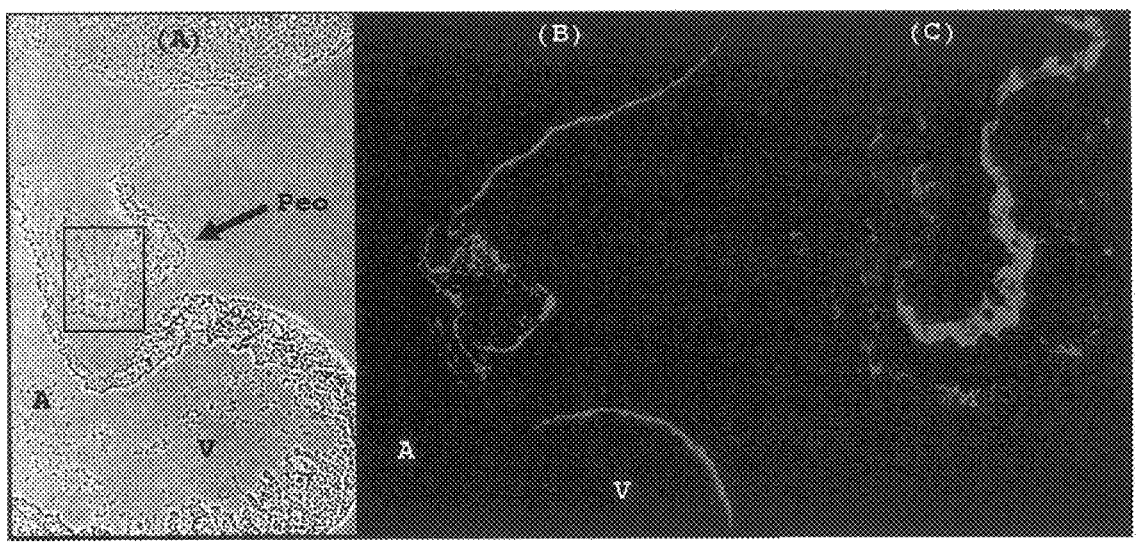
FIG. 7A is a phase contrast view of proepicardial organ (peo), developing atria (a), and ventricle (v).
FIG. 7B shows localization using anti-Bves serum demonstrating staining of proepicardial organ and the developing epicardium around the ventricle.
FIG. 7C is a high power view (130×) of migrating proepicardial strands seen in the box in FIG. 7A. The diffuse cytoplasmic distribution of Bves is noted.
Figures 8A, 8B, 8C, 8D:
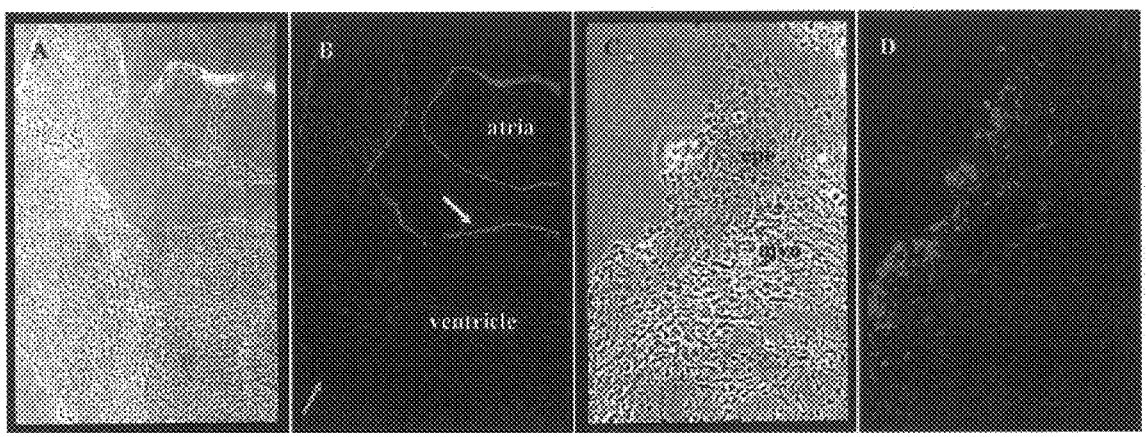
FIG. 8A is phase microscopy showing a section through the developing heart.
FIG. 8B shows that the epicardium is stained but Bves-positive cells are not yet seen in the myocardium. The white arrow shows Bves expression in cells on the dorsal side of the ventricle while the yellow arrow shows that migrating Bves-positive cells have not yet reached the ventral side of the ventricle.
FIG. 8C is phase microscopy showing an adjacent section.
FIG. 8D shows that the adjacent section was reacted with anti-Bves with competing peptide. Loss of staining is noted.
Figures 8E, 8F, 8G, 8H:
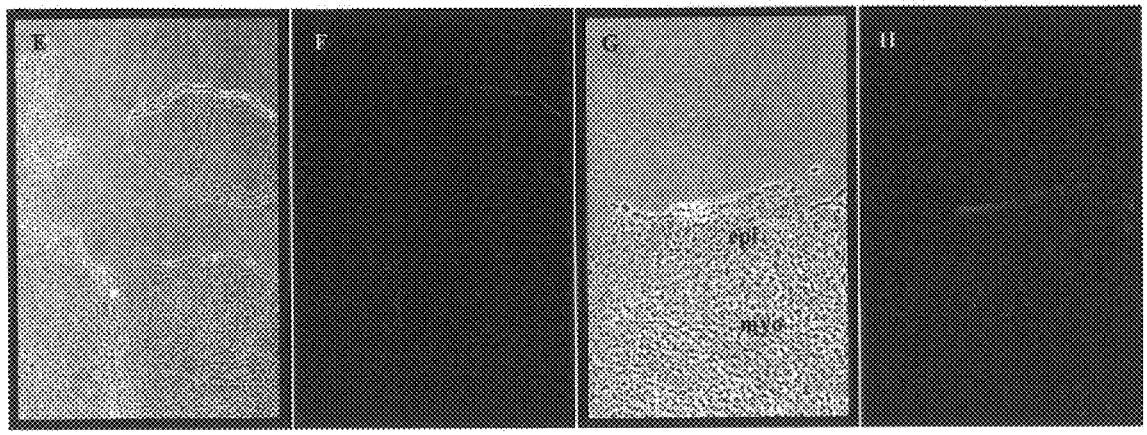
FIGS. 8E–8H are high power views (250×) of FIGS. 6A–6D (130×), respectively.
Figure 9A:
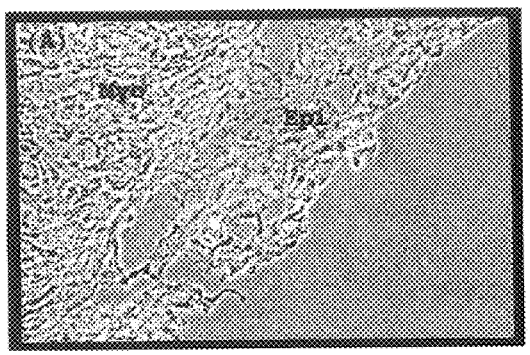
FIG. 9A is phase contrast view of the ventricular myocardium and adjacent epicardium.
Figure 9B:
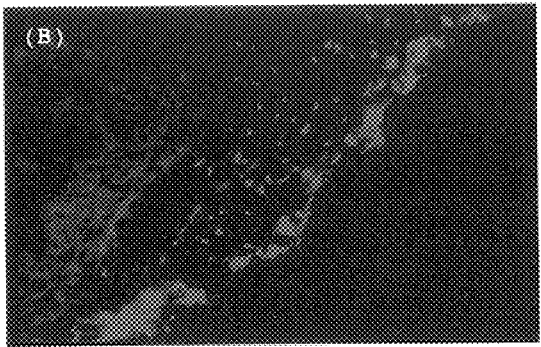
FIG. 9B shows that Bves-positive cells are localized to the epicardium as seen in red.
Figure 9C:
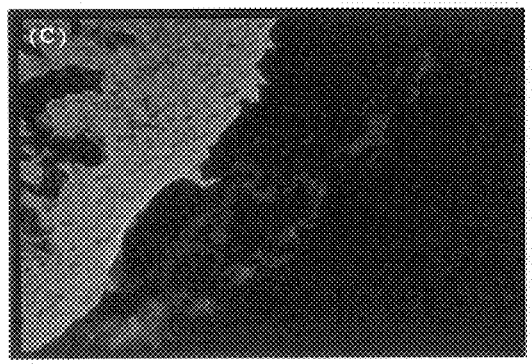
FIG. 9C shows the myocardium in green labeled by MF20.
Figure 9D:
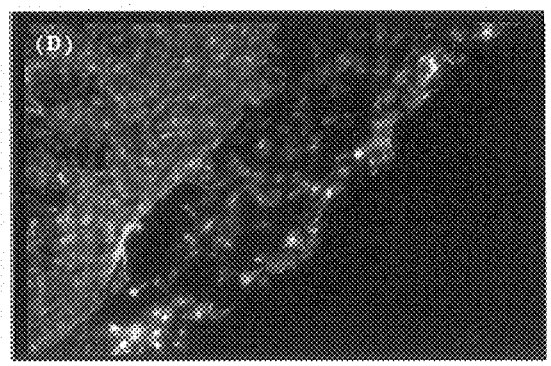
FIG. 9D shows that costaining of Bves and DAPI reveals a perinuclear localization in delaminated epicardial cells while the diffuse cytoplasmic localization is seen in the epicardium. (250×)
Figure 10A:
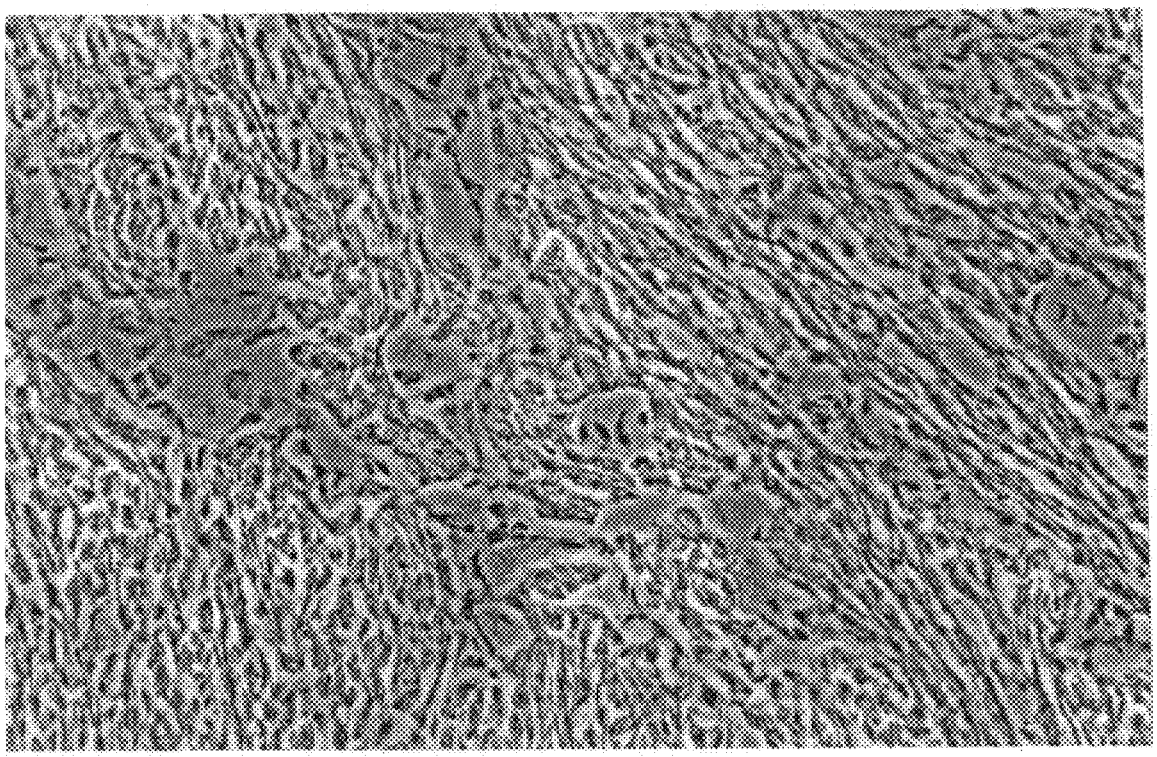
FIG. 10A shows phase contrast of E9 chick heart.
Figure 10B:
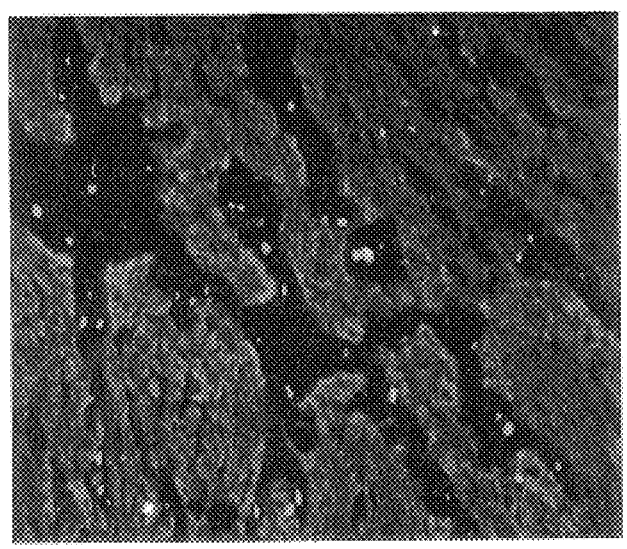
FIG. 10B shows that individual Bves-positive cells (red) are seen throughout developing channels (arrow) in the heart using MF20 (green) to denote cardiac myocytes. Note that Bves-positive cells have migrated throughout the heart.
Figure 10D:
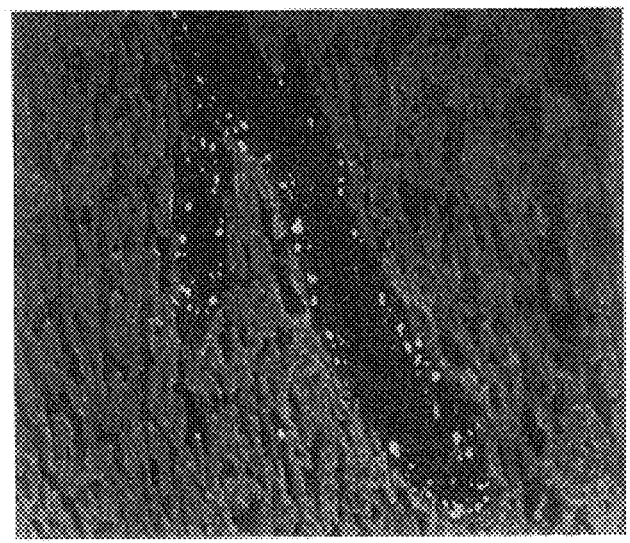
FIG. 10D shows the intracardiac vessel in an E11 chick heart labeled with the same two antibodies. Note the only Bves-positive cells are associated with the vessel (arrow). (200×)
Figure 10C:
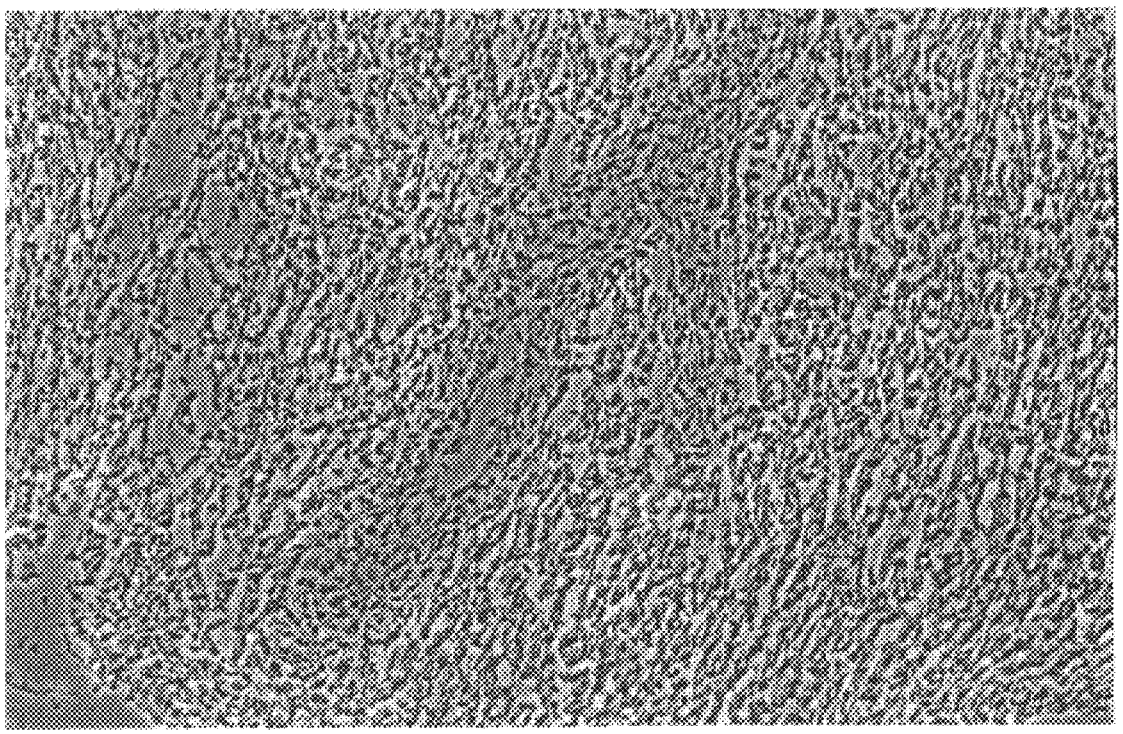
FIG. 10C is phase contrast of E11 chick heart showing a forming artery without the compacted wall.

Interestingly, immunofluorescence analysis showed that Bves was not found in heart muscle at stage 10 but instead was present in the proepicardial organ and its derivative, the migrating epicardial strands (FIG. 7B). Bves is present in proepicardial cells with wide distribution in the cytoplasm (FIG. 7C). By day 7, the epicardium has migrated over the entirety of the atria and nearly all the ventricles and is stained with anti-Bves (FIGS. 8B and 8F). Controls with prior peptide competition show complete absence of anti-Bves activity in adjacent sections (FIGS. 8D and 8H). As development proceeds, Bves-positive cells are observed in the connective tissue-rich subepicardium at E7 (FIGS. 9B and 9D). Previous studies have shown that these mesenchymal cells are derived from the proepicardial organ (Manasek, 1968; Mikawa and Gourdie, 1996; Dettman et al, 1998). The subcellular localization of Bves is dramatically altered in these delaminated cells as it takes on a punctuate, perinuclear pattern (FIG. 9D). Individual Bves-positive cells are next seen within the trabeculae of the heart wall adjacent to forming vascular channels that appear as gaps in the myocardium (FIG. 10B). As channels take on a more ordered pattern within the developing heart, Bves-positive cells are seen juxtaposed to the vascular lumen (FIG. 10D). These cells are adjacent to endothelial cells identified by QH1 staining in quail hearts. Bves-positive cells were never stained with QH1 in developing arteries. Bves expression is restricted to vascular smooth muscle of the differentiated intracardiac arteries and is not observed in systemic arteries expect for the proximal aorta (see below). These data demonstrate that Bves protein is expressed in proepicardial cells and delaminated mesenchyme and is later restricted to vascular smooth muscle cells and suggest that Bves is an early marker of smooth muscle differentiation.

EXAMPLE 15
Bves Expression Reveals Two Patterns of Vascular Smooth Muscle Differentiation As Bves appears to be an early marker of smooth muscle cell differentiation, its expression was used to analyze the differentiation of smooth muscle during vasculogenesis in the intracardiac arteries and the aorta.

Figure 11:
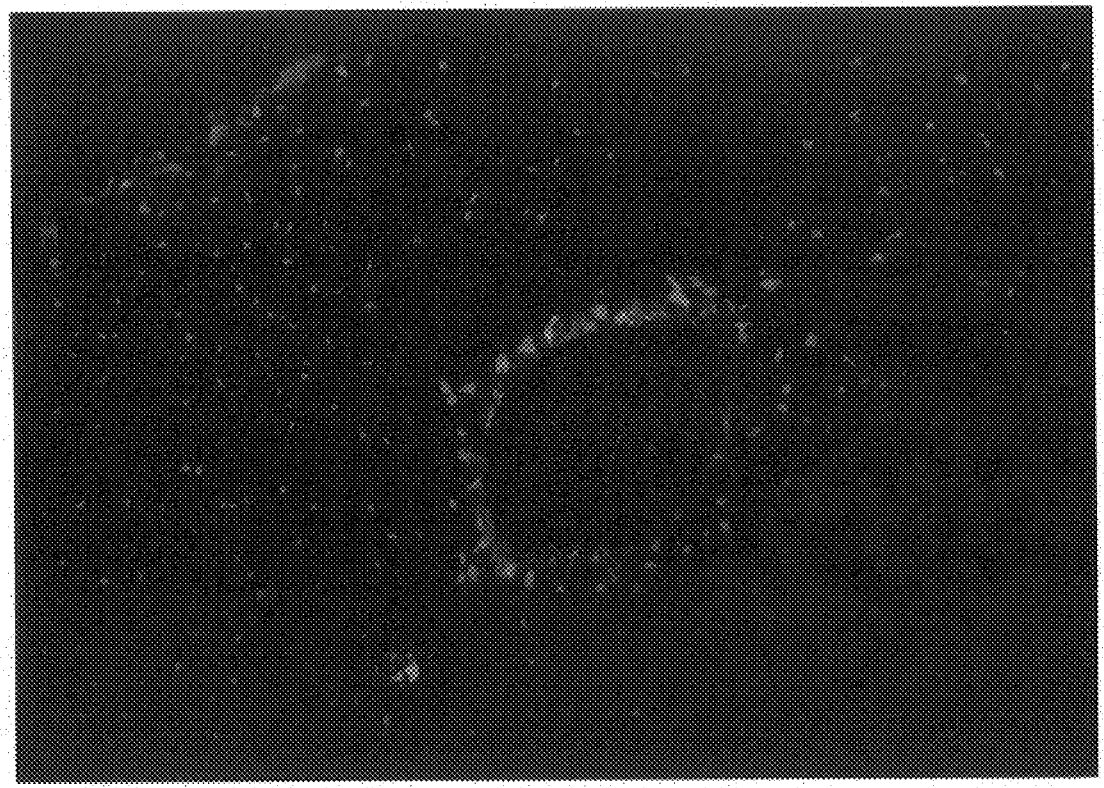
FIG. 11 shows Bves and alpha smooth muscle actin colocalization in E17 quail embryos. Bves expression (red) colocalizes with alpha smooth muscle actin (green) around a coronary artery in the E17 quail heart. Note that the smooth muscle cells closest to the lumen also express both proteins while cells that express Bves alone are added peripherally. (250×)

Analysis of arterial differentiation with Bves revealed two distinct patterns of smooth muscle differentiation. First, in intracardiac vessels including the coronaries, Bves-positive cells accumulate adjacent to the endothelium. These cells become smooth muscle actin-positive while Bves-positive, smooth muscle actin-negative cells are positioned peripherally. FIG. 11 shows the developing coronary artery as an example of intracardiac arterial differentiation. Later all vascular smooth muscle cells express both Bves and muscle contractile proteins. In contrast to the pattern seen in intracardiac vessels, concentric rings of cells closest to the luminal surface of the aorta are positive for Bves but are negative for smooth muscle actin (FIG. 12). In the more peripheral rings, cells become positive for both antisera. Thus, the pattern of expression of these two smooth muscle proteins is reversed in the aorta. Taken together, these data suggest that Bves accumulates in smooth muscle prior to contractile protein expression but that the pattern of smooth muscle differentiation is dependent upon the particular type of vessel.

EXAMPLE 16
Induction of Bves Expression by Cardiac Muscle

Figures 13A, 13B, 13C:
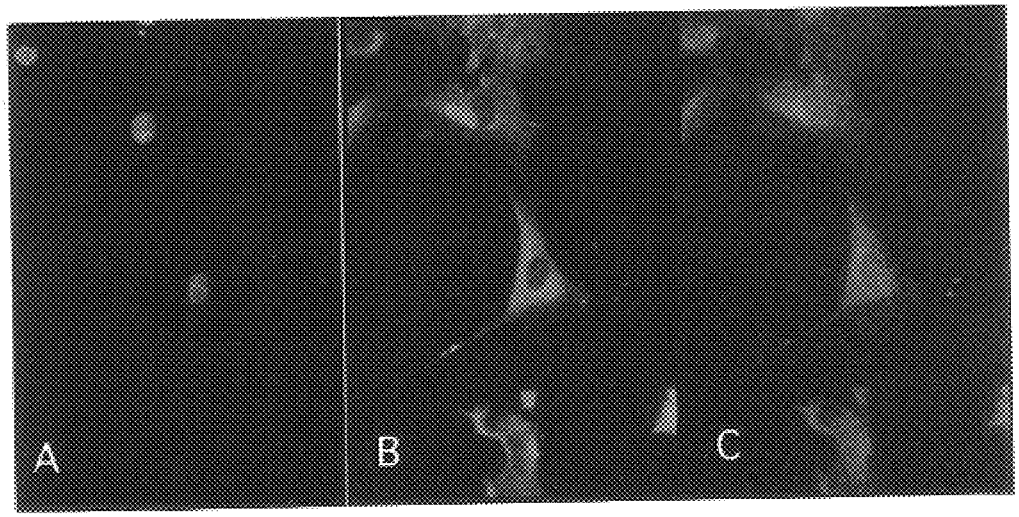
FIGS. 13A, 13B, and 13C show Bves positive proepicardial cells grown in the presence of cardiac muscle while the proepicardial cells shown in FIGS. 13D, 13E, and 13F were grown in the absence of cardiac smooth muscle.
Figures 13D, 13E, 13F:
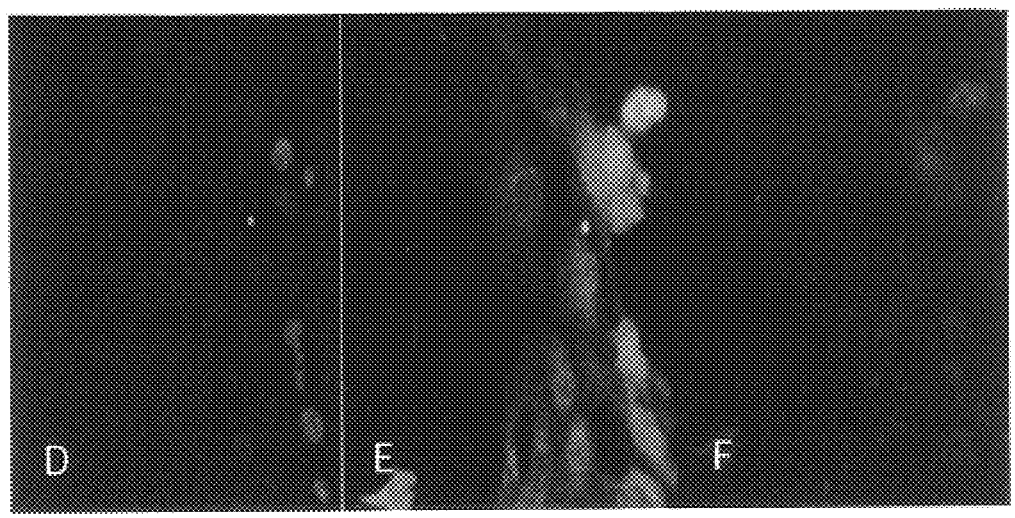

In the embryo, one of the tissues to which Bves protein localizes is the proepicardium. Additionally, unless this tissue is cultured in the presence of cardiac muscle, the proepicardial cells are not Bves positive. This induction of expression by the cardiac muscle is very important as a marker of this process. Proepicardial cells were grown in the presence (FIG. 13A–C) and absence of smooth muscle cells (FIGS. 13D–F). FIGS. 13A and 13D show the cells stained with DAPI to reveal the location of cell nuclei. FIGS. 13B and 13E show the same cells stained for alpha smooth muscle actin localization (green) to show which cells are committed to the smooth muscle lineage. FIGS. 13C and 13D show staining with D033 anti-Bves antibody. Bves-positive proepicardial cells (red) grown in the presence of cardiac muscle are shown in FIG. 13C. By comparison, Bves staining is greatly diminished in intensity in cells grown in the absence of cardiac muscle. Thus, proximity to cardiac muscle enhances Bves expression in proepicardium cells.

EXAMPLE 17
Generation of Polyclonal Antibodies Against B846 Peptide

Figure 14:
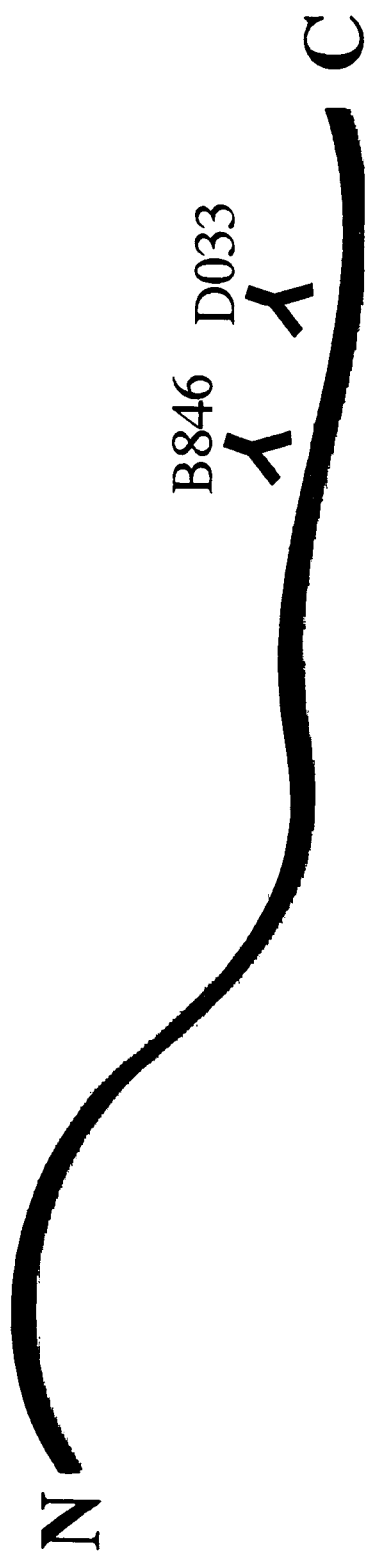
FIG. 14 shows the location of peptides used to generate the B846 and D033 antibodies relative to the primary structure of Bves.
Figure 15:
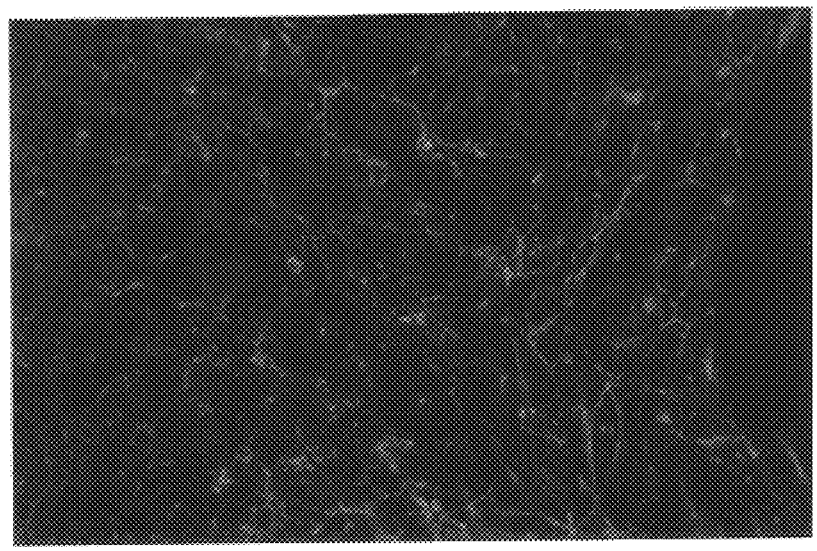
FIG. 15 shows staining of proepicardial cells grown at confluence with anti-Bves antibody B846. The red staining is from the B846 antibody while the green staining results from using a marker for tubulin.

Another antibody similar to D033 was generated using the peptide DPTLNDKKVKKLEQPQMS (SEQ ID No. 15) derived from the predicted amino acid sequence of Bves. The location of this peptide (B846) relative to the one used for generation of the D033 antibody is shown in FIG. 14. As shown in FIG. 15, the resulting B846 antibody demonstrated Bves staining in the membrane of rat epicardial cells grown at confluence (Red is staining for Bves using B846 antibody while the green results from counterstaining using a marker for tubulin). The presence of Bves in the membrane of proepicardial cells is important because Bves seems to be involved with the development of cell junctions in epithelial cells since Bves redistributes to points of cellular contact upon epithelialization.

EXAMPLE 18
Engineered Cell Line Expressing B846

Figure 16:
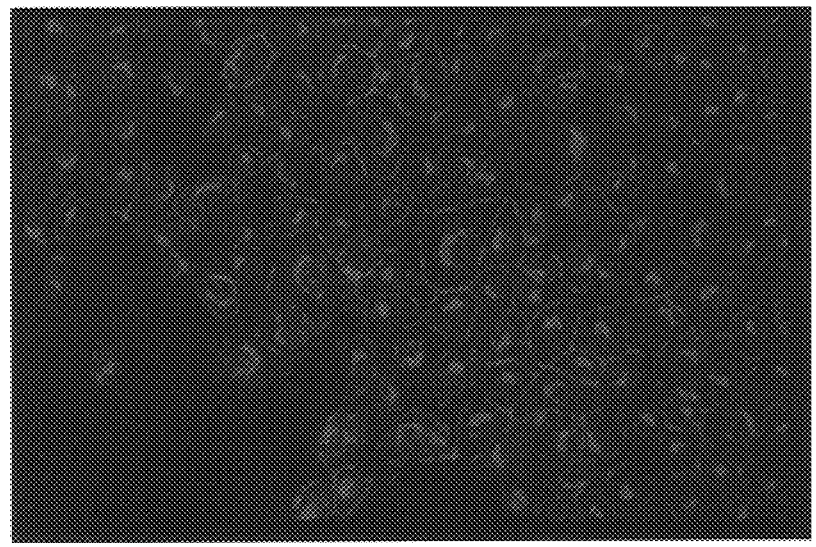
FIG. 16 shows anti-Bves staining with B846 in engineered cell line HT-1Bves. In this cell line, Bves also localizes to the membrane.

A cell line to express Bves was engineered by introducing bves cDNA driven by the CMV promoter contained in the pCINEO vector (pCINEO from Promega-commercial source). CMV promoter was chosen so that high levels of Bves expression would be maintained in HT-1 cells transfected with Bves. This allowed us to access whether the exogenous Bves would still be correctly localized to the membrane in a cell line that normally does not contain Bves. This cell line was designated HT-1Bves. Additionally, using the B846 antibody (red staining), it was demonstrated that Bves is localized to the membrane and golgi in the HT-1Bves engineered cell line (FIG. 16) in the same manner as it is localized in proepicardial cells.

Figure 17A:
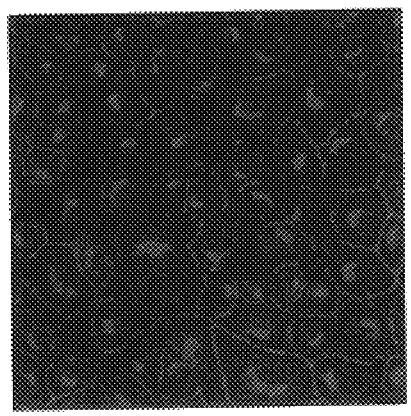
FIG. 17 shows that the subcellular distribution of Bves changes when cells contact. When epicardial cells are confluent, Anti-bves stains in both the golgi and membrane (FIG. 17A). If the cells are replated at single cell density, Bves only stains in the golgi (FIG. 17B).
FIG. 17C show the cells after the cells have regrown to confluency. When the cells touch again, Bves once again localizes at the membrane as well as the golgi.
Figure 17B:
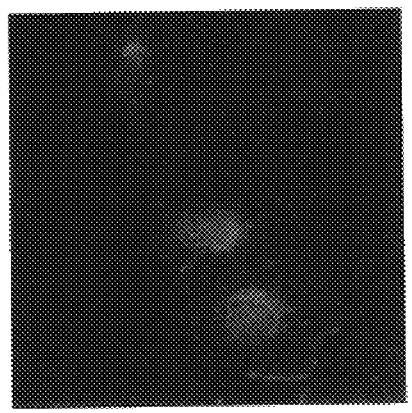
Figure 17C:
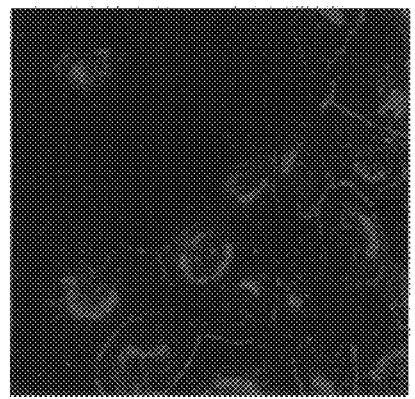

EXAMPLE 19
Bves is Involved in the Transition from Epithelial to Mesenchymal Cells The subcellular distribution of Bves changes when cells contact. As seen in FIG. 17A, when epicardial cells are confluent, anti-Bves antibody stains both the golgi and membrane. If the cells are plated at single cell density, anti-Bves only stains the golgi (FIG. 17B). FIG. 17C shows that when the cells regrown to confluency and touch again, Bves again localizes to the membrane as well as the golgi. This data suggests that Bves is involved in the development of cell-cell contacts. In the embryo, Bves changes distribution to the golgi from the membrane during mesenchyme conversion from epithelia. The same is true in culture and Bves is an early marker of this process.

Discussion

The present invention used a subtractive method to identify novel proteins expressed during cardiac morphogenesis. As a result, a novel message, bves was cloned, which is highly conserved in avians, mammals and humans. The expression pattern of Bves protein is unique during heart development as it is detected in cells of the proepicardial organ, migrating proepicardial strands, delaminated mesenchymal cells and vascular smooth muscle. Bves expression reveals the migration and patterning of cells targeted for the tunica media of intracardiac arteries. In addition, it was suggested that the initiation of smooth muscle differentiation may occur earlier than previous described and that. regulation of smooth muscle differentiation may vary in different vessels.

Chicken, mouse and human bves cDNAs have been cloned. These sequences show a remarkable degree of similarity over amino acids 70–480 suggesting a conservation of structure and function. It should be noted that this N-terminus is very proline rich while the C-terminus is predicted to have multiple potential glycosylation sites. Although these predictions are intriguing, at present, Bves cannot be assigned to any known class of proteins in the database. While Northern blot analysis suggests that bves is not widely expressed in the developing embryonic or adult chicken being present at high levels only in the heart, anti-Bves antibody detects a immunologically-related protein in smooth muscle of the small intestine. Because of its unique expression pattern, hbves may be considered as a candidate for cardiac or skeletal muscle disease genes that map to chromosome 6q21. Additional studies are underway to determine the function of Bves in the murine embryo and adult. At present, it is still unable to determine whether related proteins are expressed in the developing and adult organism. Additional biochemical analyses are necessary to determine Bves structure and function.

The present invention also demonstrates that Bves expression reveals the patterning of smooth muscle during heart vasculogenesis. Bves is expressed in cells of the proepicardial organ and migrating proepicardial strands. The proepicardial organ is a mesothelial structure positioned at the dorsal aspect of the septum transversum. At least four cell types are derived from this structure: epicardium, cardiac fibroblasts, intracardiac vascular smooth muscle and endothelium. While some cells remain as an intact epithelium, the epicardium, other cells undergo epithelial to mesenchymal transition to become progenitors of vascular endothelium, smooth muscle and cardiac fibroblasts. At present, it cannot be determined which cells of the proepicardial organ express Bves. Bves may be expressed in any or all progenitors of these four cell types while they are located in the proepicardial organ and strands but later becomes restricted to vascular smooth muscle cells.

As the proepicardial strands cover the surface of the heart, cells delaminate to form freely migratory cells (Mikawa and Gourdie, 1996; Dettman et al, 1998). Some of these cells are Bves-positive and migrate into the subepicardium and the substance of the myocardium (FIGS. 6, 8 and 9). The data in quail show that these Bves-positive cells are not QH1-positive. This suggests that delaminated Bves-positive cells are not endothelial progenitors. Bves-positive cells migrate throughout the trabecular myocardium but are only seen in the tunica media of. intracardiac arteries in differentiated hearts. Once in the media, Bves-positive cells arrange as concentric rings that eventually express other smooth muscle markers (see FIGS. 11 and 12). Thus, while it cannot be determined which cell types of the proepicardial organ transiently express Bves, Bves protein is at first broadly distributed in epicardial/epithelial cells. When the cell undergo the transformation to mesenchymal cells, Bves-positive mesenchymal cells differentiate into vascular smooth muscle cells. Bves expression in delaminated proepicardial cells and its subsequent restriction to smooth muscle cells suggests that Bves may be used as an early marker of smooth muscle cells.

Bves expression reveals novel mechanisms in vasculogenesis. The process of systemic vasculogenesis has been studied extensively. Endothelium of the systemic arterial system is derived from a continuous sheet of epithelial cells present throughout the developing embryo (Coffin and Poole, 1988). Signals from endothelium in the vascular bed are thought to recruit local mesenchyme to the smooth muscle cell lineage (reviewed in Folkman and d'Amore, 1996). Thus, the interaction of vascular endothelium and mesenchyme is essential for smooth muscle cell differentiation and vasculogenesis.

The current data and previous studies suggest that the generation of intracardiac arteries may vary from this model of vasculogenesis. First, in contrast to systemic vasculogenesis, both endothelium and smooth muscle progenitors of the intracardiac system are derived from the same epithelium, the proepicardial organ (Mikawa and Fischman, 1992; Mikawa and Gourdie, 1996; Dettman et al, 1998). These progenitors undergo concurrent migration as individual cells to spaces within the myocardium where a vascular channels form. Only later do these channels connect to form a continuous vessel (Mikawa et al, 1992; Mikawa and Gourdie, 1996). Next, the early expression of Bves suggests that progenitors of intracardiac smooth muscle, unlike systemic vasculogenesis, initiate their differentiative program prior to their arrival in the vascular bed. These cells are not fully differentiated as they have not yet expressed smooth muscle contractile proteins. Still, induction of the smooth muscle phenotype by endothelial cells may occur as the co-migration of endothelial and smooth muscle progenitors from the proepicardial organ provides ample time for their interaction. The expression of Bves in a population of delaminated proepicardial cells suggests that smooth muscle cell commitment and/or differentiation occurs much earlier in intracardiac vasculogenesis. Finally, the relationship of Bves expression with smooth muscle contractile proteins reveals variation in the differentiation of smooth muscle cells within individual developing vessels.

As seen in FIG. 11, differentiation of intracardiac vessels are characterized by the accumulation of Bves-positive cells adjacent to the developing endothelium. These cells are the first to become smooth muscle actin-positive. Other layers of Bves-positive cells are added at the periphery later becoming actin-positive thus suggesting that the most "mature" smooth muscle is juxtalumenal. This situation is like that described in the descending aorta (Hungerford et al, 1996).

In contrast, the pattern of Bves and smooth muscle actin expression in the developing aorta suggests that differentiation proceeds from outside inward with the more immature smooth muscle cells toward the lumen (see FIG. 12). In both cases, the data suggest a multistep process of smooth muscle cell differentiation. It is interesting to speculate on the potential differences in the interactions between differentiating endothelium and smooth muscle in these two vasculogenic systems. Future analysis of the regulation of Bves expression by endothelial factors may assist in the elucidation of this relationship.

The following references were cited herein.

Ausbel, et al., (1998). Current Protocols in Molecular Biology, vol. 2, Ed. Wiley press, Boston, Mass.
Bisaha, et al. (1980). Dev. Biol. 148:355–364.
Brown, et al., (1996). Dev. Biol. 174:248–257.
Coffin, et al., (1988). Development 102:735–748.
DeHaan, (1965). Morphogenesis of the vertebrate heart. In "Organogenesis" (R. L. DeHaan and H. Ursprung, Eds.), pp. 377–419. Holt Reinhardt & Winston, New York.
Dettman, et al., (1998). Dev. Biol. 193:169–181.
Fishman, et al., (1997). Development 124:2099–2117.
Folkman, et al., (1996). Cell 87:1153–1155.
Gonzalez-Sanchez, et al., (1990). Dev. Biol. 139:197–207.
Han, et al., (1992). Dev. Dyn. 193:257–265.
Hidai, H., et al., (1998). Mech. Of Dev. 73:33–43.
Hamburger, et al., (1951). J. Morphol. 88:49–92.
Hiruma, et al., (1989). Am. J. Anat. 184:129–138.
Kirby, et al., (1983). Science 220(4601):1059–1961.
Kirby, et al., (1990). Circulation 82:332–340.
Komiyama, et al., (1987). Anat. Embryol. 176:183–189.
Lu, et al., (1998). Mech. of Dev. 73:23–32.
Manasek, (1968). J. Morphol. 125:329–366.
Manner, (1993). Anat. Embryol. 187:281–289.
Mikawa, et al., (1992). Proc. Natl. Acad. Sci. U.S.A. 89:9504–9508.
Mikawa, et al., (1996). Dev. Biol. 174:221–232.
Poelmann, et al., (1993). Cir. Res. 73:559–568.
Runyan, et al., (1983). Dev. Biol. 130:167–174.
Ruzicka, et al., (1988). J. Cell Biol. 107:2575–2586.
Sater, et al., (1989). Development 206:821–830.
Shimada, et al., (1980). In "Etiology and morphogenesis of congenital heart disease" (R. van Praagh and A. Takao, Eds.), pp. 63–80. Futura, New York, N.Y.
Stanier, et al., (1992). Dev. Biol. 153:91–101.
Virágh, et al., (1981). Anat. Rec. 201:157–168.
Virágh, et al. (1993). Anat. Embryol. 188:381–393.
Wei, et al., (1996). Development 122:2779–2789.
Yutzey, et al., (1994). Development 120: 871–883.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

```
                          SEQUENCE LISTING

<160> NUMBER OF SEQ ID NOS: 15

<210> SEQ ID NO 1
<211> LENGTH: 1647
<212> TYPE: DNA
<213> ORGANISM: gallus sp.
<220> FEATURE:
<223> OTHER INFORMATION: partial cDNA sequence of chick bves (cbves)

<400> SEQUENCE: 1
gaattcaagc agggaacacg ggcgccctc  tcccttcgtc ccgcggacat caggcatcaa    60
accaccgctt cgcgccgcgg gtccacagca ccgcctcccc cgagggggaac cccgcgaccg   120 caccgggcag ccccgcagcc ccccgggcgg gcgggaggcg cctgcgcgct gcggccgctc   180
gctgtcggcc ccgggctggc gcctcccgca gcccgccggc ggttgctgcc tattttagtc   240
acagcggcgg cgggggggccg cggcgggacc ggggtcgggc ggggggctgcc ggcatcggga   300 gccgcgaaga gcgggggtcc gtgctgtcca ttcgtctggg aaactttgtc gaaggtcccg   360 ataggggggca cgggggacagg attcttcaag atggacacta cggcaatcag cccactcact   420
cctctgggcg ttattccaga cttaaaaaat gccacctctg tgcctttcaa cgagactgca   480
tgtgaaaact ggaaggagat ccatcatctt gtttttccacg tggcaaatat ttgtttttgca   540 gctggcctgg ttattccgac gactctgaac cttcatatga ttttttctgcg aggtttgctc   600 accgtaggat gtgcattgtt catcatttgg gctacactct accgttgtgc cttggacata   660
atgatctgga attctgtgtt tttggtggtc aacctttttac acttcatata cttggtgtat   720
aaaagaagac cgatcaagat agagaaagag ctcagcagcc tgtacaagag aatgtttgaa   780
ccactccatg tgcctccaga gctattccag agattaactg ggcaattctg caacattcag   840
actttgaaga caggtcaagc ttatgctgca gaggataaaa catcagttga tgacaggcta   900
agcatcctgc tgaaggggaa aatgaaggtt tcttatcgag ggcattttct gcataatatt   960
tacccctgtg cctttataga ttcacctgaa tttcgatcaa ctcagatgaa ccggggtgaa  1020
aaattccagg tcaccattat cgcagatgat aattgcaagt tcctttgctg gtccaggaa   1080 agactgacat actttctgga aactgagcca tttctttatg agatctttaa gtatctcatt  1140
ggcaaagata ttacaaataa actctattca ctgaatgacc caaccttaaa tgacaaggcc  1200
tcaaaaaaga ttgatcggca gccaagtctt tgctcacagc tctctgtgat gcagatgagg  1260
aacagtatgg ccagatccag tgacagtgag gatggcttgc agatgtttct tcgcgggact  1320
tcctcttcat cttctcttcg cccaggccgg acatcaccct acctgagaac ttcagcaaag  1380
atgaagccaa tagaggaaag cgttgaagat gacgtctttg aagcaccgtc agctgaaaag  1440
cttgagctgc agcggctgcc ttgaacgaat ctgtcatctg atggtgtaag agcttgctca  1500
aagctccagg gcgagaggaa ggaatctgga agctaagaat gtctttctgt ctttgaattt  1560
accacaccat atgtcaatgg ctcctagaca gaaatgtcac aatttttactt ctaaataaag  1620 aaataaacaa aaaaaaaaaa aaaaaaa                                      1647

<210> SEQ ID NO 2
<211> LENGTH: 1494
<212> TYPE: DNA
```

-continued

<210> ORGANISM: Mus sp.
<220> FEATURE:
<223> OTHER INFORMATION: partial cDNA sequence of mouse bves (mbves)

<400> SEQUENCE: 2

| | | | | | |
|---|---|---|---|---|---|
| gaattccacg | gagtccatcc | cgctggcaca | gtcaactgta | gcaggtttta | catctgagtt | 60 |
| agaaagtctc | acaccgtgc | cttctaatga | gaccacttgt | gagaactggc | gagagattca | 120 |
| ccatctggtt | tttcatgtag | caaacgtttg | ctttgcagtt | ggtttgctaa | ttcccaccac | 180 |
| tcttcacctc | catatgatac | tgctcagagt | gatgttgtct | ctaggatgta | ccctttatgt | 240 |
| ggtctgggcc | actctctacc | gctgtgcctt | ggatgtgatg | atctggaact | cggtgttctt | 300 |
| gggtatcaat | atttttgcatc | tttcatatct | tttgtacaag | aaaagaccgg | tcaaaattga | 360 |
| aaaggagctg | ggtggtgtct | accatcggtt | gtttgaacca | ctccgagtcc | ctccggattt | 420 |
| gtttagaagg | ttaaccggac | agttttgtat | gatccagacc | ttgaaaaggg | gccaggttta | 480 |
| cgccacagag | gacaaaacct | cagttgatga | tcgtcttagt | attctcctaa | aaggaagaat | 540 |
| gaaggtctcc | tatcgaggac | attttctgca | taacatttac | ccgtgtgcct | ttatagattc | 600 |
| tcccgaattc | agatcaacgc | agatgcacaa | aggcgaaaaa | ttccaggtca | ccattgttgc | 660 |
| agatgataac | tgcaggttct | tatgctggtc | aagagaaaga | ctgacttact | ttctggagtc | 720 |
| agagccttt | ctgtatgaaa | ttttttaggta | ccttatagga | aaagacatta | caaataagct | 780 |
| gtactcactg | aatgacccta | ctttaaatga | taagaaagtt | aagaagctgg | agccccagat | 840 |
| gagcctctgc | acacagatct | ccatgctgga | gatgaggaac | agtatcacca | gctcagcgac | 900 |
| ggcgaggacg | gcctgcacca | ctttctgcgg | ggctcctcca | gcacggcgtc | tctccccatg | 960 |
| tcctccccgc | agcagcgagc | ctctgccaag | atgaagccaa | tcgaggaagg | tagaagatga | 1020 |
| cgatgaggtc | tttgtgtctc | cagacgcact | caaagtccat | cagttgcctt | gagcggcatc | 1080 |
| tggtgaccac | gatggagctg | ccctgatgag | tgagcaggaa | aagtcccaca | ctctgttgtg | 1140 |
| acctttgggt | ggtttgcttc | agtccctcca | gagggaagt | gagggagggc | cacagacact | 1200 |
| agctgtgtgc | tacctgtcct | gtcagccagc | tccttgtgtt | agccaagcct | tctgactaga | 1260 |
| ccttgctcta | tttttgcagt | agatatatta | atattatttt | agttaatctt | aaagctatca | 1320 |
| acacaaacac | cttttcgctt | attttttctaa | gttgtggccc | atttctcatc | tctgtcatgg | 1380 |
| gaatttagaa | cgagttgttc | ttctgatcat | tttaatgatg | taagttgaaa | tcgaggctga | 1440 |
| cataacatta | aaaagtttac | cttttgttca | aaaaaaaaaa | aaaaaaaaaa | aaaa | 1494 |

<210> SEQ ID NO 3
<211> LENGTH: 1811
<212> TYPE: DNA
<213> ORGANISM: Homo sapiens
<220> FEATURE:
<223> OTHER INFORMATION: partial cDNA sequence of human bves (hbves)

<400> SEQUENCE: 3

| | | | | | |
|---|---|---|---|---|---|
| tccgccttcc | aataagacca | cttgtgaaaa | ctggagagag | atacatcatc | tggtttttca | 60 |
| tgtagcaaat | atttgttttg | cagttgggtt | ggttattcca | actactcttc | accttcatat | 120 |
| gatatttctt | aggggaatgt | taactctagg | atgtaccctt | tatatcgtct | gggccactct | 180 |
| ctaccgatgt | gccttggata | taatgatctg | gaactctgtg | ttcttgggtg | tcaacatttt | 240 |
| gcatctgtcg | tatcttttat | acaagaagag | accggtaaag | attgaaaagg | aactcagtgg | 300 |
| catgtaccgg | cgattgtttg | aaccactccg | tgtgcctcca | gatttgttca | gaagactaac | 360 |
| tggacagttt | tgcatgatcc | aaaccttgaa | aagggccaa | acttatgctg | cagaggataa | 420 |

```
aacctcagtt gatgaccgtc tgagtattct cttgaaggga aaaatgaagg tctcctatcg    480
aggacatttt ctgcataaca tttacccctg tgcctttata gattctcctg aatttagatc    540
aactcagatg cacaaaggtg aaaaattcca ggtcaccatt attgcagatg ataactgcag    600
atttttatgc tggtcaagag aaagattaac atactttctg gaatcagaac ctttcttgta    660
tgaaatcttt aggtatctta ttggaaaaga catcacaaat aagctctact cattgaatga    720
tcccacctta aatgataaga agccaaaaa gctggaacat cagctcagcc tctgcacaca     780
gatctccatg ttgaaatga ggaacagtat agccagctcc agtgacagtg acgacggctt     840
gcaccagttt cttcggggta cctccagcat gtcctctctt catgtgtcat ccccacacca    900
gcgagcctct gccaagatga aaccgataga agaaggagca aagatgatg atgacgtttt     960
tgaaccggca tctccaaata cattgaaagt ccatcagctg ccttgatcag agagagaatt   1020
caggttacca agacggaagg tgtcttgaag agatcctgaa aaataccagc acttttcat    1080
ggcttttagg ttattctgct ttagtgcatc cagactggta gagtcggagg gaggaagtga   1140
ggaagggtca aggatggaag agttctttca cttacccttt ttattagtca gcttttaaag   1200
taattgtttt actgagcctt ctgactatgc cttgttctct tttgagatat atattttcac   1260
agtcttttct agatatatta ttgttttaac ttaacaaatc ttagcaatct ctcaatgcct   1320
tttcacttat ttttttccaa gttatgattc tttttcctca cagtctttt tgttccatag    1380
caatgaggtt gtccatttga taatttaac aaacaatgta agtttaaaat tgaggctaag    1440
gtaacatgaa aaagcaggga atctcaaact ttattccata tattattcac acacacacac   1500
acacacacac acacacacac atacagaggc tgtttccata gggacagagc accgcagtgt   1560
gagagaggat tgggctggga ctgagaaggg cgttcctgct gtggtgaggc agccctcagg   1620
gtctctcctg gcacacagct gccagcgtga tggggatcc cttcagaata gcagcaaaac    1680
ccacgatact gaggagtaac tcaaaccaaa cttgtgggtc tcacagagag gatatcgtct   1740
tgcccatgta aagattcctt ttagatggtt tctggtgttt actaatgttg ttaataggtg   1800
tattttcgg a                                                         1811
```

<210> SEQ ID NO 4  
<211> LENGTH: 487  
<212> TYPE: PRT  
<213> ORGANISM: gallus sp.  
<220> FEATURE:  
<223> OTHER INFORMATION: predicted amino acid sequence of chick Bves

<400> SEQUENCE: 4

Glu Phe Lys Gln Gly Thr Arg Ala Pro Leu Ser Leu Arg Pro Ala
                5                  10                  15

Asp Ile Arg His Gln Thr Thr Ala Ser Arg Arg Gly Ser Thr Ala
                20                  25                  30

Pro Pro Pro Pro Arg Gly Thr Pro Arg Pro His Arg Ala Ala Pro
                35                  40                  45

Gln Pro Pro Gly Arg Ala Gly Gly Ala Cys Ala Leu Arg Pro Leu
                50                  55                  60

Ala Val Gly Pro Gly Leu Ala Pro Pro Ala Ala Arg Arg Arg Leu
                65                  70                  75

Leu Pro Ile Leu Val Thr Ala Ala Ala Gly Gly Arg Gly Gly Thr
                80                  85                  90

Gly Val Gly Arg Gly Leu Pro Ala Ser Gly Ala Ala Lys Ser Gly
                95                  100                 105

```
Gly Pro Cys Cys Pro Phe Val Trp Glu Thr Leu Ser Lys Val Pro
            110                 115                 120

Ile Gly Gly Thr Gly Thr Gly Phe Phe Lys Met Asp Thr Thr Ala
            125                 130                 135

Ile Ser Pro Leu Thr Pro Leu Gly Val Ile Pro Asp Leu Lys Asn
            140                 145                 150

Ala Thr Ser Val Pro Phe Asn Glu Thr Ala Cys Glu Asn Trp Lys
            155                 160                 165

Glu Ile His His Leu Val Phe His Val Ala Asn Ile Cys Phe Ala
            170                 175                 180

Ala Gly Leu Val Ile Pro Thr Thr Leu Asn Leu His Met Ile Phe
            185                 190                 195

Leu Arg Gly Leu Leu Thr Val Gly Cys Ala Leu Phe Ile Ile Trp
            200                 205                 210

Ala Thr Leu Tyr Arg Cys Ala Leu Asp Ile Met Ile Trp Asn Ser
            215                 220                 225

Val Phe Leu Val Val Asn Leu Leu His Phe Ile Tyr Leu Val Tyr
            230                 235                 240

Lys Arg Arg Pro Ile Lys Ile Glu Lys Glu Leu Ser Ser Leu Tyr
            245                 250                 255

Lys Arg Met Phe Glu Pro Leu His Val Pro Pro Glu Leu Phe Gln
            260                 265                 270

Arg Leu Thr Gly Gln Phe Cys Asn Ile Gln Thr Leu Lys Thr Gly
            275                 280                 285

Gln Ala Tyr Ala Ala Glu Asp Lys Thr Ser Val Asp Asp Arg Leu
            290                 295                 300

Ser Ile Leu Leu Lys Gly Lys Met Lys Val Ser Tyr Arg Gly His
            305                 310                 315

Phe Leu His Asn Ile Tyr Pro Cys Ala Phe Ile Asp Ser Pro Glu
            320                 325                 330

Phe Arg Ser Thr Gln Met Asn Arg Gly Glu Lys Phe Gln Val Thr
            335                 340                 345

Ile Ile Ala Asp Asp Asn Cys Lys Phe Leu Cys Trp Ser Arg Glu
            350                 355                 360

Arg Leu Thr Tyr Phe Leu Glu Thr Glu Pro Phe Leu Tyr Glu Ile
            365                 370                 375

Phe Lys Tyr Leu Ile Gly Lys Asp Ile Thr Asn Lys Leu Tyr Ser
            380                 385                 390

Leu Asn Asp Pro Thr Leu Asn Asp Lys Ala Ser Lys Lys Ile Asp
            395                 400                 405

Arg Gln Pro Ser Leu Cys Ser Gln Leu Ser Val Met Gln Met Arg
            410                 415                 420

Asn Ser Met Ala Arg Ser Ser Asp Ser Glu Asp Gly Leu Gln Met
            425                 430                 435

Phe Leu Arg Gly Thr Ser Ser Ser Ser Leu Arg Pro Gly Arg
            440                 445                 450

Thr Ser Pro Tyr Leu Arg Thr Ser Ala Lys Met Lys Pro Ile Glu
            455                 460                 465

Glu Ser Val Glu Asp Asp Val Phe Glu Ala Pro Ser Ala Glu Lys
            470                 475                 480

Leu Glu Leu Gln Arg Leu Pro
            485
```

```
<210> SEQ ID NO 5
<211> LENGTH: 330
<212> TYPE: PRT
<213> ORGANISM: Mus sp.
<220> FEATURE:
<223> OTHER INFORMATION: predicted amino acid sequence of mouse Bves

<400> SEQUENCE: 5

Asn Ser Thr Glu Ser Ile Pro Leu Ala Gln Ser Thr Val Ala Gly
                 5                  10                  15

Phe Thr Ser Glu Leu Glu Ser Leu Thr Pro Val Pro Ser Asn Glu
                20                  25                  30

Thr Thr Cys Glu Asn Trp Arg Glu Ile His His Leu Val Phe His
                35                  40                  45

Val Ala Asn Val Cys Phe Ala Val Gly Leu Leu Ile Pro Thr Thr
                50                  55                  60

Leu His Leu His Met Ile Leu Leu Arg Val Met Leu Ser Leu Gly
                65                  70                  75

Cys Thr Leu Tyr Val Val Trp Ala Thr Leu Tyr Arg Cys Ala Leu
                80                  85                  90

Asp Val Met Ile Trp Asn Ser Val Phe Leu Gly Ile Asn Ile Leu
                95                 100                 105

His Leu Ser Tyr Leu Leu Tyr Lys Lys Arg Pro Val Lys Ile Glu
               110                 115                 120

Lys Glu Leu Gly Gly Val Tyr His Arg Leu Phe Glu Pro Leu Arg
               125                 130                 135

Val Pro Pro Asp Leu Phe Arg Arg Leu Thr Gly Gln Phe Cys Met
               140                 145                 150

Ile Gln Thr Leu Lys Arg Gly Gln Val Tyr Ala Thr Glu Asp Lys
               155                 160                 165

Thr Ser Val Asp Asp Arg Leu Ser Ile Leu Leu Lys Gly Arg Met
               170                 175                 180

Lys Val Ser Tyr Arg Gly His Phe Leu His Asn Ile Tyr Pro Cys
               185                 190                 195

Ala Phe Ile Asp Ser Pro Glu Phe Arg Ser Thr Gln Met His Lys
               200                 205                 210

Gly Glu Lys Phe Gln Val Thr Ile Val Ala Asp Asp Asn Cys Arg
               215                 220                 225

Phe Leu Cys Trp Ser Arg Glu Arg Leu Thr Tyr Phe Leu Glu Ser
               230                 235                 240

Glu Pro Phe Leu Tyr Glu Ile Phe Arg Tyr Leu Ile Gly Lys Asp
               245                 250                 255

Ile Thr Asn Lys Leu Tyr Ser Leu Asn Asp Pro Thr Leu Asn Asp
               260                 265                 270

Lys Lys Val Lys Leu Glu Pro Gln Met Ser Leu Cys Thr Gln
               275                 280                 285

Ile Ser Met Leu Glu Met Arg Asn Ser Ile Thr Ser Ser Ala Thr
               290                 295                 300

Ala Arg Thr Ala Cys Thr Thr Phe Cys Gly Ala Pro Pro Ala Arg
               305                 310                 315

Arg Leu Ser Pro Cys Pro Pro Arg Ser Ser Glu Pro Leu Pro Arg
               320                 325                 330

<210> SEQ ID NO 6
<211> LENGTH: 334
```

```
<212> TYPE: PRT
<213> ORGANISM: Homo sapiens
<220> FEATURE:
<223> OTHER INFORMATION: predicted amino acid sequence of human Bves

<400> SEQUENCE: 6

Pro Pro Ser Asn Lys Thr Thr Cys Glu Asn Trp Arg Glu Ile His
                 5                  10                  15

His Leu Val Phe His Val Ala Asn Ile Cys Phe Ala Val Gly Leu
                20                  25                  30

Val Ile Pro Thr Thr Leu His Leu His Met Ile Phe Leu Arg Gly
                35                  40                  45

Met Leu Thr Leu Gly Cys Thr Leu Tyr Ile Val Trp Ala Thr Leu
                50                  55                  60

Tyr Arg Cys Ala Leu Asp Ile Met Ile Trp Asn Ser Val Phe Leu
                65                  70                  75

Gly Val Asn Ile Leu His Leu Ser Tyr Leu Leu Tyr Lys Lys Arg
                80                  85                  90

Pro Val Lys Ile Glu Lys Glu Leu Ser Gly Met Tyr Arg Arg Leu
                95                  100                 105

Phe Glu Pro Leu Arg Val Pro Pro Asp Leu Phe Arg Arg Leu Thr
                110                 115                 120

Gly Gln Phe Cys Met Ile Gln Thr Leu Lys Lys Gly Gln Thr Tyr
                125                 130                 135

Ala Ala Glu Asp Lys Thr Ser Val Asp Asp Arg Leu Ser Ile Leu
                140                 145                 150

Leu Lys Gly Lys Met Lys Val Ser Tyr Arg Gly His Phe Leu His
                155                 160                 165

Asn Ile Tyr Pro Cys Ala Phe Ile Asp Ser Pro Glu Phe Arg Ser
                170                 175                 180

Thr Gln Met His Lys Gly Glu Lys Phe Gln Val Thr Ile Ile Ala
                185                 190                 195

Asp Asp Asn Cys Arg Phe Leu Cys Trp Ser Arg Glu Arg Leu Thr
                200                 205                 210

Tyr Phe Leu Glu Ser Glu Pro Phe Leu Tyr Glu Ile Phe Arg Tyr
                215                 220                 225

Leu Ile Gly Lys Asp Ile Thr Asn Lys Leu Tyr Ser Leu Asn Asp
                230                 235                 240

Pro Thr Leu Asn Asp Lys Lys Ala Lys Lys Leu Glu His Gln Leu
                245                 250                 255

Ser Leu Cys Thr Gln Ile Ser Met Leu Glu Met Arg Asn Ser Ile
                260                 265                 270

Ala Ser Ser Ser Asp Ser Asp Gly Leu His Gln Phe Leu Arg
                275                 280                 285

Gly Thr Ser Ser Met Ser Ser Leu His Val Ser Ser Pro His Gln
                290                 295                 300

Arg Ala Ser Ala Lys Met Lys Pro Ile Glu Glu Gly Ala Glu Asp
                305                 310                 315

Asp Asp Asp Val Phe Glu Pro Ala Ser Pro Asn Thr Leu Lys Val
                320                 325                 330

His Gln Leu Pro

<210> SEQ ID NO 7
<211> LENGTH: 340
<212> TYPE: PRT
```

<213> ORGANISM: Mus sp.
<220> FEATURE:
<221> NAME/KEY: DOMAIN
<223> OTHER INFORMATION: derived amino acid sequence of mouse Bves
      carboxyl domain

<400> SEQUENCE: 7

```
Met Asn Ser Thr Glu Ser Ile Pro Leu Ala Gln Ser Thr Val Ala
                 5                  10                  15

Gly Phe Thr Ser Glu Leu Glu Ser Leu Thr Pro Val Pro Ser Asn
                20                  25                  30

Glu Thr Thr Cys Glu Asn Trp Arg Glu Ile His His Leu Val Phe
                35                  40                  45

His Val Ala Asn Val Cys Phe Ala Val Gly Leu Leu Ile Pro Thr
                50                  55                  60

Thr Leu His Leu His Met Ile Leu Leu Arg Val Met Leu Ser Leu
                65                  70                  75

Gly Cys Thr Leu Tyr Val Val Trp Ala Thr Leu Tyr Arg Cys Ala
                80                  85                  90

Leu Asp Val Met Ile Trp Asn Ser Val Phe Leu Gly Ile Asn Ile
                95                 100                 105

Leu His Leu Ser Tyr Leu Leu Tyr Lys Lys Arg Pro Val Lys Ile
               110                 115                 120

Glu Lys Glu Leu Gly Gly Val Tyr His Arg Leu Phe Glu Pro Leu
               125                 130                 135

Arg Val Pro Pro Asp Leu Phe Arg Arg Leu Thr Gly Gln Phe Cys
               140                 145                 150

Met Ile Gln Thr Leu Lys Arg Gly Gln Val Tyr Ala Thr Glu Asp
               155                 160                 165

Lys Thr Ser Val Asp Asp Arg Leu Ser Ile Leu Leu Lys Gly Arg
               170                 175                 180

Met Lys Val Ser Tyr Arg Gly His Phe Leu His Asn Ile Tyr Pro
               185                 190                 195

Cys Ala Phe Ile Asp Ser Pro Glu Phe Arg Ser Thr Gln Met His
               200                 205                 210

Lys Gly Glu Lys Phe Gln Val Thr Ile Val Ala Asp Asp Asn Cys
               215                 220                 225

Arg Phe Leu Cys Trp Ser Arg Glu Arg Leu Thr Tyr Phe Leu Glu
               230                 235                 240

Ser Glu Pro Phe Leu Tyr Glu Ile Phe Arg Tyr Leu Ile Gly Lys
               245                 250                 255

Asp Ile Thr Asn Lys Leu Tyr Ser Leu Asn Asp Pro Thr Leu Asn
               260                 265                 270

Asp Lys Lys Val Lys Lys Leu Glu Pro Gln Met Ser Leu Cys Thr
               275                 280                 285

Gln Ile Ser Met Leu Glu Met Arg Asn Ser Ile Thr Ser Ser Ser
               290                 295                 300

Asp Gly Glu Asp Gly Leu His His Phe Leu Arg Gly Ser Ser Ser
               305                 310                 315

Thr Ala Ser Leu Pro Met Ser Ser Pro Gln Gln Arg Ala Ser Ala
               320                 325                 330

Lys Met Lys Pro Ile Glu Glu Gly Arg Arg
               335                 340
```

<210> SEQ ID NO 8

-continued

```
<211> LENGTH: 357
<212> TYPE: PRT
<213> ORGANISM: gallus sp.
<220> FEATURE:
<221> NAME/KEY: DOMAIN
<223> OTHER INFORMATION: derived amino acid sequence of chick Bves
      carboxyl domain

<400> SEQUENCE: 8

Met Asp Thr Thr Ala Ile Ser Pro Leu Thr Pro Leu Gly Val Ile
                  5                  10                  15

Pro Asp Leu Lys Asn Ala Thr Ser Val Pro Phe Asn Glu Thr Ala
                 20                  25                  30

Cys Glu Asn Trp Lys Glu Ile His His Leu Val Phe His Val Ala
                 35                  40                  45

Asn Ile Cys Phe Ala Ala Gly Leu Val Ile Pro Thr Thr Leu Asn
                 50                  55                  60

Leu His Met Ile Phe Leu Arg Gly Leu Leu Thr Val Gly Cys Ala
                 65                  70                  75

Leu Phe Ile Ile Trp Ala Thr Leu Tyr Arg Cys Ala Leu Asp Ile
                 80                  85                  90

Met Ile Trp Asn Ser Val Phe Leu Val Val Asn Leu Leu His Phe
                 95                 100                 105

Ile Tyr Leu Val Tyr Lys Arg Arg Pro Ile Lys Ile Glu Lys Glu
                110                 115                 120

Leu Ser Ser Leu Tyr Lys Arg Met Phe Glu Pro Leu His Val Pro
                125                 130                 135

Pro Glu Leu Phe Gln Arg Leu Thr Gly Gln Phe Cys Asn Ile Gln
                140                 145                 150

Thr Leu Lys Thr Gly Gln Ala Tyr Ala Ala Glu Asp Lys Thr Ser
                155                 160                 165

Val Asp Asp Arg Leu Ser Ile Leu Leu Lys Gly Lys Met Lys Val
                170                 175                 180

Ser Tyr Arg Gly His Phe Leu His Asn Ile Tyr Pro Cys Ala Phe
                185                 190                 195

Ile Asp Ser Pro Glu Phe Arg Ser Thr Gln Met Asn Arg Gly Glu
                200                 205                 210

Lys Phe Gln Val Thr Ile Ile Ala Asp Asp Asn Cys Lys Phe Leu
                215                 220                 225

Cys Trp Ser Arg Glu Arg Leu Thr Tyr Phe Leu Glu Thr Glu Pro
                230                 235                 240

Phe Leu Tyr Glu Ile Phe Lys Tyr Leu Ile Gly Lys Asp Ile Thr
                245                 250                 255

Asn Lys Leu Tyr Ser Leu Asn Asp Pro Thr Leu Asn Asp Lys Ala
                260                 265                 270

Ser Lys Lys Ile Asp Arg Gln Pro Ser Leu Cys Ser Gln Leu Ser
                275                 280                 285

Val Met Gln Met Arg Asn Ser Met Ala Arg Ser Ser Asp Ser Glu
                290                 295                 300

Asp Gly Leu Gln Met Phe Leu Arg Gly Thr Ser Ser Ser Ser Ser
                305                 310                 315

Leu Arg Pro Gly Arg Thr Ser Pro Tyr Leu Arg Thr Ser Ala Lys
                320                 325                 330

Met Lys Pro Ile Glu Glu Ser Val Glu Asp Val Phe Glu Ala
                335                 340                 345
```

Pro Ser Ala Glu Lys Leu Glu Leu Gln Arg Leu Pro
            350                 355

<210> SEQ ID NO 9
<211> LENGTH: 23
<212> TYPE: DNA
<213> ORGANISM: Artificial sequence
<220> FEATURE:
<221> NAME/KEY: primer_bind
<223> OTHER INFORMATION: 5' primer sequence from mouse bves used to
      clone human bves

<400> SEQUENCE: 9
tttgaaccac tccgagtccc tcc                                           23

<210> SEQ ID NO 10
<211> LENGTH: 22
<212> TYPE: DNA
<213> ORGANISM: Artificial sequence
<220> FEATURE:
<221> NAME/KEY: primer_bind
<223> OTHER INFORMATION: 3' primer sequence from mouse bves used to
      clone human bves

<400> SEQUENCE: 10
tgaccagcat aagaacctgc ag                                            22

<210> SEQ ID NO 11
<211> LENGTH: 20
<212> TYPE: DNA
<213> ORGANISM: Artificial sequence
<220> FEATURE:
<221> NAME/KEY: primer_bind
<223> OTHER INFORMATION: bves specific primer for RT-PCR analysis

<400> SEQUENCE: 11
aaccactcca tgtgcctcca                                               20

<210> SEQ ID NO 12
<211> LENGTH: 20
<212> TYPE: DNA
<213> ORGANISM: Artificial sequence
<220> FEATURE:
<221> NAME/KEY: primer_bind
<223> OTHER INFORMATION: bves specific primer for RT-PCR analysis

<400> SEQUENCE: 12
ctgcgataat ggtgacctgg                                               20

<210> SEQ ID NO 13
<211> LENGTH: 891
<212> TYPE: DNA
<213> ORGANISM: Artificial sequence
<220> FEATURE:
<223> OTHER INFORMATION: 3' probe generated from mbves cDNA,
      corresponding to the 3' UTR and 3' most portion of the mbves ORF,
      used for in situ hybridization

<400> SEQUENCE: 13
gaattcagat caacgcagat gcacaaaggc gaaaaattcc aggtcaccat tgttgcagat    60
gataactgca ggttcttatg ctggtcaaga gaaagactga cttactttct ggagtcagag   120 cctttctgt atgaaatttt taggtaccct ataggaaaag acattacaaa taagctgtac    180
tcactgaatg accctacttt aaatgataag aaagttaaga agctggagcc ccagatgagc   240
ctctgcacac agatctccat gctggagatg aggaacagta tcaccagctc cagcgacggc   300

```
gaggacggcc tgcaccactt tctgcggggc tcctccagca cggcgtctct ccccatgtcc      360
tccccgcagc agcgagcctc tgccaagatg aagccaatcg aggaaggtag aagatgacga      420
tgaggtcttt gtgtctccag acgcactcaa agtccatcag ttgccttgag cggcatctgg      480
tgaccacgat ggagctgccc tgatgagtga gcaggagaag tcccacactc tgttgtgacc      540
tttgggtggt ttgcttcagt ccctccagaa gggaagtgag ggagggccac agacactagc      600
tgtgtgctac ctgtcctgtc agccagctcc ttgtgttagc caagccttct gactagacct      660
tgctctattt ttgcagtaga tatattaata ttattttagt taatcttaaa gctatcaaca      720
caaacacctt ttcgcttatt tttctaagtt gtggcccatt tctcatctct gtcatgggaa      780
tttagaacga gttgttcttc tgatcatttt aatgatgtaa gttgaaatcg aggctgacat      840
aacattaaaa agtttacctt ttgttcaaaa aaaaaaaaaa aaaaaaaaa a                891
```

<210> SEQ ID NO 14
<211> LENGTH: 15
<212> TYPE: PRT
<213> ORGANISM: Artificial sequence
<220> FEATURE:
<221> NAME/KEY: PEPTIDE
<223> OTHER INFORMATION: sequence of chick Bves peptide used for
      generating polyclonal antibody D033

<400> SEQUENCE: 14

Asp Ser Pro Glu Phe Arg Ser Thr Gln Met Asn Arg Gly Glu Lys
              5                   10                  15

<210> SEQ ID NO 15
<211> LENGTH: 18
<212> TYPE: PRT
<213> ORGANISM: Artificial sequence
<220> FEATURE:
<221> NAME/KEY: PEPTIDE
<223> OTHER INFORMATION: sequence of Bves peptide used for generating
      polyclonal antibody B846

<400> SEQUENCE: 15

Asp Pro Thr Leu Asn Asp Lys Lys Val Lys Lys Leu Glu Gln Pro
              5                   10                  15

Gln Met Ser

What is claimed is:

1. An isolated polynucleotide and its complementary strand, wherein said polynucleotide encodes a blood vessel/epicardial substance protein, Bves, and said polynucleotide is selected from the group consisting of:
   (a) a polynucleotide having the sequence shown in SEQ ID No. 3 which encodes said Bves protein; and
   (b) a polynucleotide differing from the nucleic acids of (a) in codon sequence due to the degeneracy of the genetic code, and which encodes said Bves protein.

2. The polynucleotide of claim 1, wherein said polynucleotide is expressed in developing adult heart and skeletal muscle cells in an organism selected from the group consisting of chick, mouse and human.

3. The polynucleotide of claim 1, wherein said Bves protein has the amino acid sequence of SEQ ID No. 6.

4. An expression vector comprising the polynucleotide of claim 1 and regulatory elements necessary for expressing said Bves protein encoded by said polynucleotide in a cell.

5. A host cell transfected with the vector of claim 4.

6. The host cell of claim 5, wherein said host cell is selected from the group consisting of a bacterial cell, animal cell, plant cell and insect cell.

7. The host cell of claim 6, wherein said bacterial cell is *E coli*.

8. The host cell of claim 8, wherein said animal cell is a human T-cell lymphoblastic lymphoma cell line.

* * * * *